(12) United States Patent
Clark et al.

(10) Patent No.: US 8,691,944 B2
(45) Date of Patent: Apr. 8, 2014

(54) FIBRONECTIN POLYPEPTIDES AND METHODS OF USE

(75) Inventors: Richard A. Clark, Poqnott, NY (US); Xiang-Dong Ren, Malvern, PA (US); Fubao Lin, Stony Brook, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 1310 days.

(21) Appl. No.: 12/089,291

(22) PCT Filed: Oct. 4, 2006

(86) PCT No.: PCT/US2006/038778
§ 371 (c)(1),
(2), (4) Date: Oct. 9, 2008

(87) PCT Pub. No.: WO2007/044396
PCT Pub. Date: Apr. 19, 2007

(65) Prior Publication Data
US 2009/0111738 A1 Apr. 30, 2009

Related U.S. Application Data

(60) Provisional application No. 60/723,496, filed on Oct. 4, 2005.

(51) Int. Cl.
*A61K 38/00* (2006.01)
*A61K 38/10* (2006.01)

(52) U.S. Cl.
USPC .......................................... 530/326; 514/21.5

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,522,811 A | 6/1985 | Eppstein et al. | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 4,939,239 A | 7/1990 | Matsuhashi et al. | |
| 5,051,448 A | 9/1991 | Shashoua | |
| 5,053,388 A | 10/1991 | Gibson et al. | |
| 5,166,320 A | 11/1992 | Wu et al. | |
| 5,169,862 A | 12/1992 | Burke, Jr. et al. | |
| 5,192,746 A | 3/1993 | Lobl et al. | |
| 5,270,168 A | 12/1993 | Grinnell | |
| 5,283,173 A | 2/1994 | Fields et al. | |
| 5,288,514 A | 2/1994 | Ellman | |
| 5,359,115 A | 10/1994 | Campbell et al. | |
| 5,362,899 A | 11/1994 | Campbell | |
| 5,453,489 A * | 9/1995 | Ruoslahti et al. | 530/350 |
| 5,539,085 A | 7/1996 | Bischoff et al. | |
| 5,559,103 A | 9/1996 | Gaeta et al. | |
| 5,576,423 A | 11/1996 | Aversa et al. | |
| 6,799,657 B2 | 10/2004 | Daniels | |
| 6,808,923 B2 | 10/2004 | Engelman et al. | |
| 6,818,209 B1 | 11/2004 | Mitrophanous et al. | |
| 6,830,892 B2 | 12/2004 | Marasco et al. | |
| 6,863,884 B2 | 3/2005 | Schauber et al. | |
| 6,924,123 B2 | 8/2005 | Kingsman et al. | |
| 7,105,341 B2 | 9/2006 | Kinsella | |
| 2003/0027751 A1* | 2/2003 | Kovesdi et al. | 514/12 |
| 2004/0120918 A1 | 6/2004 | Lintner et al. | |
| 2005/0008604 A1 | 1/2005 | Schultz et al. | |
| 2005/0025725 A1 | 2/2005 | Schultz et al. | |
| 2005/0282747 A1 | 12/2005 | Clark et al. | |
| 2006/0038778 A1 | 2/2006 | Boon et al. | |

FOREIGN PATENT DOCUMENTS

| | | |
|---|---|---|
| JP | 07-113623 | 5/1995 |
| WO | WO91/07087 | 5/1991 |
| WO | WO92/10092 | 6/1992 |
| WO | WO93/09668 | 5/1993 |
| WO | WO93/20242 | 10/1993 |
| WO | WO94/08051 | 4/1994 |
| WO | WO2005009510 | 3/2005 |
| WO | WO2005117936 | 12/2005 |
| WO | WO2007044396 | 4/2007 |

OTHER PUBLICATIONS

Ming Yi and Erkki Ruoslahti, A fibronectin inhibits tumor growth, angiogenesis and metastasis. PNAS, vol. 98 No. 2, 620-624 Jan. 16, 2001.*
Ambesi et al., "Anastelin, a fragment of the first type III repeat of fibronectin, inhibits extracellular signal-regulated kinase and causes G(I) arrest in human microvessel endothelial cells", Cancer Res. 65:148-156, 2005.
Clark et al., "Fibronectin and fibrin provide a provisional matrix of epidermal cell migration during wound reepithelialization", J. Invest. Dermatol., 79:264-269, 1982.
Clark et al., "Blood vessel fibronectin increases in conjunction with endothelial cell proliferation and capillary ingrowth during wound healing", J. Invest. Dermatol. 79:269-276, 1982.
Clark et al., "Fibronectin is produced by blood vessels in response to injury", J. Exp. Med. 156:646-651, 1982.
Clark et al., "Fibronectin beneath reepithelializing epidermis in vivo: Sources and significance", J. Invest. Dermatol. 80 (suppl.):26S-30S, 1983.
Clark et al., "Either exogenous or endogenous fibronectin can promote adherence of human endothelial cells", J. Cell Sci. 82:263-280, 1986.
Clark et al., "Collagen matrices attenuate the collagen synthetic response of cultured fibroblasts to TGF-β", J. Cell Sci. 108:1251-1261, 1995.
Clark et al., "Fibroblast migration on fibronectin requires 3 distinct functional domains", J. Invest. Dermatol. 121:695-705, 2003.

(Continued)

*Primary Examiner* — Christina Bradley
*Assistant Examiner* — Jeanette Lieb
(74) *Attorney, Agent, or Firm* — Duane Morris, LLP; Lee Crews

(57) ABSTRACT

Described herein are fragments of fibronectin and variants thereof that bind growth factors. Compositions containing such a fragment of fibronectin are therefore useful in sequestering growth factors, and complexes containing both a FN fragment and a bound, active growth factor can be used to deliver growth factors to a patient (e.g., to a wound on the patient's skin).

12 Claims, 4 Drawing Sheets

(56) References Cited

OTHER PUBLICATIONS

Danilenko et al., "Growth factors in porcine full and partial thickness burn repair", Am. J. Pathol., 147:1261-1277, 1995.

Galit and Clark, "Studies in vitro on the role of 60 v and β1 integrins in the adhesion of human dermal fibroblasts to provisional matrix proteins fibronectin, vitronectin, and fibrinogen", J. Invest. Dermatol. 106:102-108, 1996.

Garcia et al., "Modulation of cell proliferation and differentiation through substrate-dependent changes in fibronectin conformation", Mol. Biol. Cell 10:785-798, 1999.

Greenhalgh et al., "PDGF and FGF stimulate wound healing in the genetically diabetic mouse", Am. J. Path. 136:1235-1246, 1990.

Greiling and Clark, "Fibronectin provides a conduit for fibroblast transmigration from a collagen gel into a fibrin gel", J. Cell Sci. 110(Pt. 7):861-870, 1997.

Grinnell et al., "Degradation of fibronectin and vitronectin in chronic wound fluid: analysis by cell blotting, immunoblotting, and cell adhesion assays", J. Invest. Dermatol. 98:410-416, 1992.

Gui et al., "Identification of the heparin-binding determinants within fibronectin repeat III", J. Biol. Chem. 281:34816-34825, 2006.

Maile et al., "The Heparin binding domain of vitronectin is the region that is required to enhance Insulin-like Growth Factor-I signaling", Mol. Endocrinol. 20:881-892, 2006.

Miyamoto et al., "Integrins can collaborate with growth factors for phosphorylation of receptor tyrosine kinases and MAP kinase activation: roles of integrin aggregation and occupancy of receptors", J. Cell Biol. 135:1633-1642, 1996.

Wijelath et al., "Novel vascular endothelial growth factor binding domains of fibronectin enhance vascular endothelial growth factor biological activity", Circ. Res. 91:25-31, 2002.

Wijelath et al., Heparin-II domain of fibronectin is a vascular endothelial growth factor-binding domain, Cir. Res. 99:853-860, 2006.

Xu and Clark, "Extracellular matrix alters PDGF regulation of fibroblast integrins", J. Cell Biol. 132:239-249, 1996.

* cited by examiner

FIGURE 1: Human Plasma Fibronectin (FN)

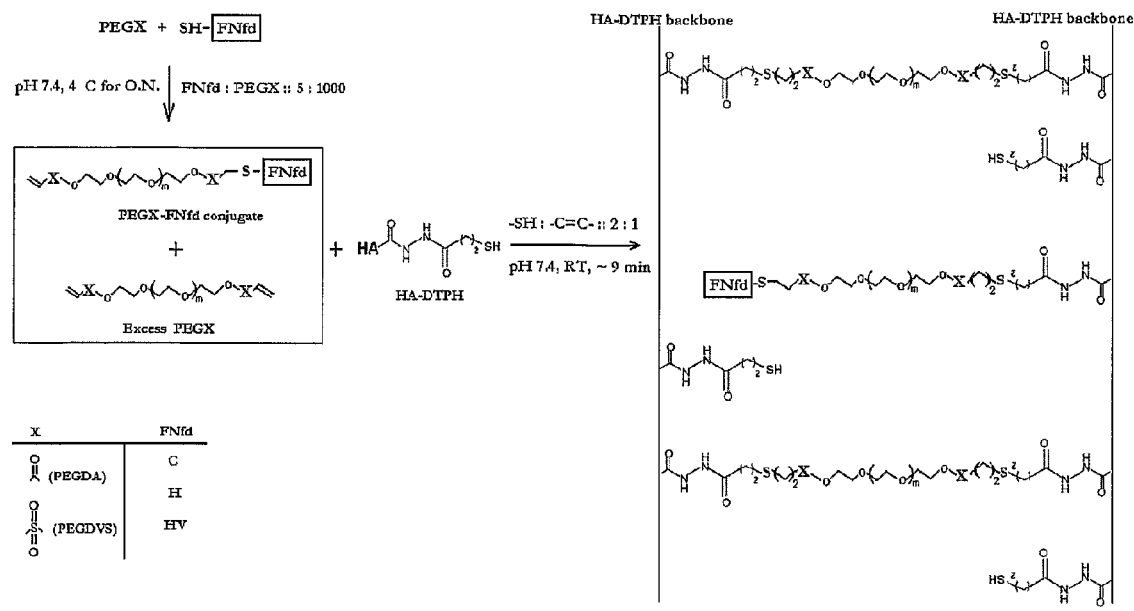
FIGURE 3 : Formulation of synECM hydrogels

The sequence of P02751 (FINC_HUMAN)(Cold-insoluble globulin)
In one-letter code:

```
             1          11         21         31         41         51
        MLRGPGPGLL LLAVQCLGTA VPSTGASKSK RQAQQMVQPQ SPVAVSQSKP GCYDNGKHYQ
  61    INQQWERTYL GNALVCTCYG GSRGFNCESK PEAEETCFDK YTGNTYRVGD TYERPKDSMI
 121    WDCTCIGAGR GRISCTIANR CHEGGQSYKI GDTWRRPHET GGYMLECVCL GNGKGEWTCK
 181    PIAEKCFDHA AGTSYVVGET WEKPYQGWMM VDCTCLGEGS GRITCTSRNR CNDQDTRTSY
 241    RIGDTWSKKD NRGNLLQCIC TGNGRGEWKC ERHTSVQTTS SGSGPFTDVR AAVYQPQPHP
 301    QPPPYGHCVT DSGVVYSVGM QWLKTQGNKQ MLCTCLGNGV SCQETAVTQT YGGNSNGEPC
 361    VLPFTYNGRT FYSCTTEGRQ DGHLWCSTTS NYEQDQKYSF CTDHTVLVQT QGGNSNGALC
 421    HFPFLYNNHN YTDCTSEGRR DNMKWCGTTQ NYDADQKFGF CPMAAHEEIC TTNEGVMYRI
 481    GDQWDKQHDM GHMMRCTCVG NGRGEWTCIA YSQLRDQCIV DDITYNVNDT FHKRHEEGHM
 541    LNCTCFGQGR GRWKCDPVDQ CQDSETGTFY QIGDSWEKYV HGVRYQCYCY GRGIGEWHCQ
 601    PLQTYPSSSG PVEVFITETP SQPNSHPIQW NAPQPSHISK YILRWRPKNS VGRWKEATIP
 661    GHLNSYTIKG LKPGVVYEGQ LISIQQYGHQ EVTRFDFTTT STSTPVTSNT VTGETTPFSP
 721    LVATSESVTE ITASSFVVSW VSASDTVSGF RVEYELSEEG DEPQYLDLPS TATSVNIPDL
 781    LPGRKYIVNV YQISEDGEQS LILSTSQTTA PDAPPDPTVD QVDDTSIVVR WSRPQAPITG
 841    YRIVYSPSVE GSSTELNLPE TANSVTLSDL QPGVQYNITI YAVEENQEST PVVIQQETTG
 901    TPRSDTVPSP RDLQFVEVTD VKVTIMWTPP ESAVTGYRVD VIPVNLPGEH GQRLPISRNT
 961    FAEVTGLSPG VTYYFKVFAV SHGRESKPLT AQQTTKLDAP TNLQFVNETD STVLVRWTPP
1021    RAQITGYRLT VGLTRRGQPR QYNVGPSVSK YPLRNLQPAS EYTVSLVAIK GNQESPKATG
1081    VFTTLQPGSS IPPYNTEVTE TTIVITWTPA PRIGFKLGVR PSQGGEAPRE VTSDSGSIVV
1141    SGLTPGVEYV YTIQVLRDGQ ERDAPIVNKV VTPLSPPTNL HLEANPDTGV LTVSWERSTT
1201    PDITGYRITT TPTNGQQGNS LEEVVHADQS SCTFDNLSPG LEYNVSVYTV KDDKESVPIS
1261    DTIIPAVPPP TDLRFTNIGP DTMRVTWAPP PSIDLTNFLV RYSPVKNEED VAELSISPSD
1321    NAVVLTNLLP GTEYVVSVSS VYEQHESTPL RGRQKTGLDS PTGIDFSDIT ANSFTVHWIA
1381    PRATITGYRI RHHPEHFSGR PREDRVPHSR NSITLTNLTP GTEYVVSIVA LNGREESPLL
1441    IGQQSTVSDV PRDLEVVAAT PTSLLISWDA PAVTVRYYRI TYGETGGNSP VQEFTVPGSK
1501    STATISGLKP GVDYTITVYA VTGRGDSPAS SKPISINYRT EIDKPSQMQV TDVQDNSISV
1561    KWLPSSSPVT GYRVTTTPKN GPGPTKTKTA GPDQTEMTIE GLQPTVEYVV SVYAQNPSGE
1621    SQPLVQTAVT NIDRPKGLAF TDVDVDSIKI AWESPQGQVS RYRVTYSSPE DGIHELFPAP
1681    DGEEDTAELQ GLRPGSEYTV SVVALHDDME SQPLIGTQST AIPAPTDLKF TQVTPTSLSA
1741    QWTPPNVQLT GYRVRVTPKE KTGPMKEINL APDSSSVVVS GLMVATKYEV SVYALKDTLT
1801    SRPAQGVVTT LENVSPPRRA RVTDATETTI TISWRTKTET ITGFQVDAVP ANGQTPIQRT
1861    IKPDVRSYTI TGLQPGTDYK IYLYTLNDNA RSSPVVIDAS TAIDAPSNLR FLATTPNSLL
1921    VSWQPPRARI TGYIIKYEKP GSPPREVVPR PRPGVTEATI TGLEPGTEYT IYVIALKNNQ
1981    KSEPLIGRKK TDELPQLVTL PHPNLHGPEI LDVPSTVQKT PFVTHPGYDT GNGIQLPGTS
2041    GQQPSVGQQM IFEEHGFRRT TPPTTATPIR HRPRPYPPNV GEEIQIGHIP REDVDYHLYP
2101    HGPGLNPNAS TGQEALSQTT ISWAPFQDTS EYIISCHPVG TDEEPLQFRV PGTSTSATLT
2161    GLTRGATYNI IVEALKDQQR HKVREEVVTV GNSVNEGLNQ PTDDSCFDPY TVSHYAVGDE
2221    WERMSESGFK LLCQCLGFGS GHFRCDSSRW CHDNGVNYKI GEKWDRQGEN GQMMSCTCLG
2281    NGKGEFKCDP HEATCYDDGK TYHVGEQWQK EYLGAICSCT CFGGQRGWRC DNCRRPGGEP
2341    SPEGTTGQSY NQYSQRYHQR TNTNVNCPIE CFMPLDVQAD REDSRE
```

Figure 4

FIBRONECTIN POLYPEPTIDES AND METHODS OF USE

RELATED APPLICATION

This application claims the benefit of priority under 35 U.S.C. § 371 of International Application No. PCT/US2006/038778, filed on Oct. 4, 2006, which claims the benefit of priority of U.S. Provisional Application No. 60/723,496, which was filed on Oct. 4, 2005. The contents of the prior international and provisional applications are hereby incorporated by reference herein in their entirety.

GOVERNMENT SUPPORT

The work described below was supported at least in part by a grant from the U.S. Government (National Institutes of Health grant AR10143). The U.S. government may, therefore, have certain rights in the invention.

TECHNICAL FIELD

This invention relates to polypeptides derived from fibronectin and, more particularly, to fibronectin polypeptides that bind growth factors and that are useful in, for example, the treatment of wounds and cancer.

BACKGROUND

There is evidence that fibronectin is involved in many biological processes including tissue repair, embryogenesis, blood clotting, cell migration, wound repair, and cell adhesion. There are two primary forms of fibronectin. The first is an insoluble glycoprotein dimer that serves as a linker in the extracellular matrix (ECM), and the second is a soluble disulfide-linked dimer found in plasma. The ECM form of fibronectin is expressed by fibroblasts, chondrocytes, endothelial cells, macrophages and certain epithelial cells. The plasma form of fibronectin is expressed by hepatocytes. Fibronectin can serve as a general cell adhesion molecule by anchoring cells to collagen or to proteoglycan substrates. Fibronectin can also play a role in organizing cellular interactions by binding to components of the ECM and to membrane-bound fibronectin receptors on cell surfaces. Forms of fibronectin are found in vertebrates, including mammals, birds, amphibians, fish, and reptiles.

SUMMARY

Recently, we discovered, inter alia, that fragments of fibronectin (FN), including fragments within domains $FNIII_{1-2}$, H and HV, promiscuously bind growth factors and that those growth factors retain functional activity when bound. Accordingly, the invention features compositions (e.g., physiologically acceptable compositions) that include a fragment of a fibronectin (e.g., a human fibronectin such as a human plasma fibronectin or ECM fibronectin) that binds a polypeptide growth factor (GF). Further, one or more of the biological activities of the bound GFs can be either retained or enhanced. For example, where a GF exerts a positive effect on a biological process, such as wound healing, its biological activity would be retained or enhanced when bound to a FN fragment as described herein when the bound GF continues to exert a positive effect on the same biological process. The effect may be as great or greater than that exerted by the unbound GF, but it may also be less.

While the fragment of fibronectin or the growth factor can be naturally occurring (i.e., either can have a sequence found in any species in any isoform), either or both of these components can also be biologically active variants of a naturally occurring fibronectin or growth factor, respectively (e.g., their sequence can differ from that of a naturally occurring FN or GF sequence). Similarly, the glycosylation pattern may be that of a naturally occurring fibronectin or GF or may be altered due, for example, to expression in a heterologous cell (e.g., a bacterial cell). A biologically active variant of a FN fragment described herein is one that, for example, functions as a GF-binding polypeptide and functions to a useful extent and in substantially the same manner as the corresponding FN fragment. For example, where a FN fragment having a naturally occurring sequence binds a GF with a particular affinity and, upon administration to a patient, effectively carries or delivers that GF to a site where the GF is needed, a biologically active variant of that FN fragment will be one that, although not identical to the FN fragment, will bind the same GF(s) with sufficiently useful affinity and similarly deliver the GF(s) to a site of need. For ease of reading, we do not repeat the term "or a biologically active variant thereof" after every reference to a FN fragment, GF, or other protein or peptide. It is to be understood that where FN fragments having a naturally occurring sequence are useful, so are biologically active variants of those fragments. The same is true with reference to growth factors and other proteins or polypeptides.

In various embodiments, the polypeptide growth factor can be a transforming growth factor-β1 (TGF-β1), a transforming growth factor β2 (TGF-β2), a basic fibroblast growth factor (bFGF), a fibroblast growth factor 7 (FGF-7), a platelet-derived growth factor (PDGF-BB), a vascular endothelial growth factor A (VEGF-A), a nerve growth factor (NGF), or any combination or sub-combination thereof. The polypeptide growth factor or a variant thereof can have or retain biological activity (e.g., one or more of its known or discovered activities) when bound by the fragment of fibronectin (e.g., plasma fibronectin).

The fragment of fibronectin can be derived from any species or type of fibronectin. For example, the fibronectin can be a human fibronectin, such as a human plasma fibronectin. Reference may be made to various fibronectin sequences, including precursor sequences that include signal sequences (e.g., precursor plasma fibronectins). One of ordinary skill in the art will recognize that the absolute position of a FN polypeptide within a FN protein can vary depending on, for example, the species of FN or the form (e.g., whether a leader or pre-pro sequence is present or whether the FN sequence is fused to another sequence (e.g., a sequence that extends the circulating half-life of the FN polypeptide, such as an albumin or a portion of an immunoglobulin (e.g., the Fc region of an IgG))). Polypeptides derived from various forms of FN and various modified forms thereof (e.g., biologically active mutants and FN polypeptide-containing complexes, as described further below) can be used in the present compositions and methods.

With respect to length, a fragment of fibronectin can have about, or less than about, 500 (e.g., no more than 498, 488, 478, 468, 458, 448, 438, or 428), 400 (e.g., no more than 398, 388, 378, 368, 358, 348, 338, or 328), 300 (e.g., no more than 298, 288, 278, 268, 258, 248, 238, or 228), 200 (e.g., no more than 198, 188, 178, 168, 158, 148, 138, or 128), 100, 75, 50, 45, 40, 35, 30, 28, 27, 26, or 25 amino acid residues. For example, the fragment can include no more than 26 amino acid residues (e.g., no more than 26 amino acid residues that are identical to 26 contiguous amino acid residues found in a naturally occurring fibronectin protein). With respect to sequence, a fragment of fibronectin can have a sequence normally found within the region designated $FNIII_1$, $FNIII_2$, $FNIII_{12-14}$, $FNIII_{12-V15}$ (HV) or IIICS. A fragment of fibronectin can have or can include a sequence normally found within the region designated $FNIII_{1-2}$ or a portion thereof; $FNIII_1$ or a portion thereof; $FNIII_2$ or a portion thereof; $FNIII_{12-V15}$ or a portion thereof; $FNIII_{12-15}$ or a portion thereof; $FNIII_{12-14}$ or a portion thereof; $FNIII_{12-13}$ or a portion thereof; $FNIII_{13-14}$ or a portion thereof; IIICS or a portion thereof. The portions may be as short as 3-10 amino acid residues (e.g., 4, 5, 6, 7, or 8 contiguous residues). With respect to function, a fragment can bind a polypeptide growth factor with an affinity of at least or about $1 \times 10^{-7}$ M (e.g., at least $1 \times 10^{-8}$ M).

Where a biologically active fragment of fibronectin is used, the fragment can be at least or about 80% identical (e.g., at least or about 85%, 90%, 95%, 98%, or 99% identical) to a corresponding wild type fragment of fibronectin.

More specifically, and in accordance with a consensus sequence based on some of the useful fragments of fibronectin we discovered, the compositions of the present invention can include a fragment of fibronectin or a biologically active variant thereof that has an amino acid sequence conforming to Formula I:

$Xaa_1$-$Xaa_2$-$Xaa_3$-$Xaa_4$-$Xaa_5$-$Xaa_6$-$Xaa_7$-$Xaa_8$-$Xaa_9$-

$Xaa_{10}$-$Xaa_{11}$-$Xaa_{12}$-$Xaa_{13}$-$Xaa_{14}$-$Xaa_{15}$-$Xaa_{16}$-$Xaa_{17}$-

$Xaa_{18}$-$Xaa_{19}$ (Formula I)

In Formula I, $Xaa_1$ can be Gln or Asn (e.g., Gln); $Xaa_2$ can be any one or two amino acid residues (e.g., Pro, Leu-Ile, or Gly); $Xaa_3$ can be Ser or Thr (e.g., Ser); $Xaa_4$ can be absent or any single amino acid residue (e.g., $Xaa_4$ can be absent, His, or Val); $Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four or five amino acid residues (e.g., Leu-Arg-Trp-Arg (SEQ ID NO:17)); $Xaa_{11}$ can be absent or any single amino acid residue (e.g., $Xaa_{11}$ can be absent or Pro); $Xaa_{12}$ can be Lys or Arg (e.g., Lys); $Xaa_{13}$ can be any one or two amino acid residues (e.g., Asn-Ser); $Xaa_{14}$ can be any one or two amino acid residues (e.g., Val-Gly); $Xaa_{15}$ can be Arg or Thr (e.g., Arg); $Xaa_{16}$ can be any one or two amino acid residues (e.g., Trp); $Xaa_{17}$ can be Lys, Gln, Thr, or Ser (e.g., Lys); $Xaa_{18}$ can be any two amino acid residues (e.g., Glu-Ala); and $Xaa_{19}$ can be Thr. In certain embodiments, certain provisos may apply. For example, the fragment of fibronectin, where identical to a portion of a naturally occurring fibronectin, may not be WNAPQPSHIS-KYILRWRPKNSVGRWKEATIPGHLNSY-TIKGLKPGVVYEGQLISIQ QYGHQEVTRFD-FTTTSTST (SEQ ID NO: 2) or may not be more than at least or about 40%, 50%, or 60% of this sequence(i.e., of SEQ ID NO: 2).

The fragment of fibronectin can include or can consist of QPSHISKYILRWRPKNSVGRWKEAT (SEQ ID NO: 3); QLISIQQYGHQEVTRFDFTTTSTST (SEQ ID NO: 4); NGQTPIQRTIKPDVRSYTITGLQPGT (SEQ ID NO: 5); or QPSVGQQMIFEEHGFRRTTPPTTAT (SEQ ID NO: 6). Where the fragment of fibronectin includes these sequences, or any of the naturally occurring fragments of fibronectin described herein, it is to be understood that the use of the term "fragment" excludes a full-length fibronectin protein.

The sequences listed above are derived from a human plasma fibronectin. Alternatively, or in addition, one can use a non-plasma FN (e.g., ECM FN) or corresponding plasma or non-plasma sequences of FN that are not derived from a human (e.g., fragments having a corresponding sequence from any fibronectin isoform of any FN-expressing species). This is the case with respect to any of the polypeptides described herein (not just those conforming to Formula I). For example, the FN polypeptide can be that of a vertebrate, such as a non-human mammal (e.g., a non-human primate), a bird, an amphibian, a fish, or a reptile. These sequences are known in the art and readily available. In some instances, the sequences, or biologically active variants thereof, derived from one species may be identical to those derived from another species. In any event, a corresponding sequence will be apparent to one of ordinary skill in the art.

In other embodiments, the fragment of fibronectin used in one or more of the various compositions described herein, or biologically active variants thereof, can have, or can include, an amino acid sequence conforming to Formula II:

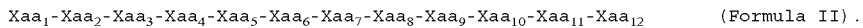

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$ (Formula II).

In Formula II, $Xaa_1$ can be Gln or Asn (e.g., Gln); $Xaa_2$ can be any amino acid residue (e.g., Pro); $Xaa_3$ can be Ser or Thr (e.g., Ser); $Xaa_4$ can be any amino acid residue (e.g., His); $Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four amino acid residues (e.g., Leu-Arg-Trp-Arg (SEQ ID NO:17)); $Xaa_{11}$ can be any amino acid residue (e.g., Pro); and $Xaa_{12}$ can be Lys or Arg (e.g., Lys). For example, the compositions of the invention can include a fragment of fibronectin that has, or that includes, the sequence QPSHIS-KYILRWRPK (SEQ ID NO: 7). Those of ordinary skill in the art will easily recognize and understand the use of both the three-letter and single-letter codes used to refer to amino acid residues.

In other embodiments, the fragment of fibronectin used in one or more of the various compositions described herein, or biologically active variants thereof, can have, or can include, an amino acid sequence conforming to Formula III:

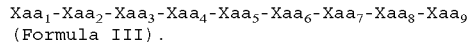

$Xaa_1$-$Xaa_2$-$Xaa_3$-$Xaa_4$-$Xaa_5$-$Xaa_6$-$Xaa_7$-$Xaa_8$-$Xaa_9$ (Formula III).

In Formula III, $Xaa_1$ can be Ile or Gly (e.g., Ile); $Xaa_2$ can be any four or five amino acid residues and $Xaa_3$ can be absent or any single amino acid residue (e.g., $Xaa_2$ can be Leu-Arg-Trp-Arg-Pro (SEQ ID NO:18) and $Xaa_3$ can be absent or $Xaa_2$ can be Leu-Arg-Trp-Arg (SEQ ID NO: 17) and $Xaa_3$ can be Pro); $Xaa_4$ can be Lys or Arg (e.g., Lys); $Xaa_5$ can any one or two amino acid residues (e.g., Asn-Ser); $Xaa_6$ can be any one or two amino acid residues (e.g., Val-Gly); $Xaa_7$ can be Arg or Thr (e.g., Arg); $Xaa_8$ can be any one or two amino acid residues (e.g., Trp); and $Xaa_9$ can be Lys, Gln, Thr, or Ser (e.g., Lys). For example, the compositions of the invention can include a fragment of fibronectin that has, or that includes, the sequence ILRWRPKNSVGRWK (SEQ ID NO: 8).

As noted, the fragments of fibronectin useful in the present compositions can include an amino acid sequence that is identical to a sequence within a naturally occurring fibronectin or they can include a biologically active variant thereof. These sequences can be modified at, for example, either the amino terminus, the carboxy terminus, or both. For example, the fragments can include at least two cysteine residues, one or both of which are, optionally, at the C-terminal or N-terminal of the fragment. For example, a fragment can include a naturally occurring fibronectin-derived sequence having at or near each of the C- and N-termini, a cysteine residue. The fragment can be cyclized by formation of a disulfide bond between these two cysteine residues (or, more generally, between two of the at least two cysteine residues present at the terminal regions). While the peptides of the present invention may be linear or cyclic, cyclic peptides generally have an advantage over linear peptides in that their cyclic structure is more rigid and hence their biological activity may be higher than that of the corresponding linear peptide (see, generally, Veber et al., Nature 292:55-58, 1981). Any method for cyclizing peptides can be applied to the FN fragments described herein.

Alternatively, or in addition, the fragment can further include a substituent at the amino-terminus or carboxy-terminus. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons). The acyl group can be a lower acyl group (e.g., an acyl group having up to four carbon atoms), especially an acetyl group.

As noted, the fragments can vary in length and can be or can include contiguous amino acid residues that naturally occur in fibronectin or that vary to a certain degree from a naturally occurring fibronectin sequence (but retain a biological activity). Where the fragments include, at their N-terminus or C-terminus (or both), amino acid residues that are not naturally found in fibronectin, the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 150, 160, 170, 180, 190, or 200 residues, and one terminus can include none (e.g., it can terminate in an amino acid sequence identical to a naturally occurring fibronectin sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues. Where biologically active variants of a FN fragment are used, the variant can vary by substitution of one or more amino acid residues within these groups. The variants can include a conservative amino acid substitution.

The fragments of fibronectin, including the modified fragments described above, can be protease resistant and can include one or more types of protecting groups such as an acyl group, an amide group, a benzyl or benzoyl group, or a polyethylene glycol. More specifically, a fragment of fibronectin, including the modified fragments described above, can be N-terminally acetylated and/or C-terminally amidated.

The fragments of fibronectin can also be modified in order to improve absorption, including for example, an addition of sugar residues to enhance transport across the blood-brain barrier.

Any of the fragments of fibronectin can include at least one amino acid residue in the D-form. Any of the fragments of fibronectin can include at least one non-naturally occurring or modified amino acid residue (e.g., 4-hydroxyproline, gamma-carboxyglutamic acid, o-phosphoserine, o-phosphotyrosine, or delta-hydroxylysine). Non-naturally occurring amino acid residues are amino acid residues other than the 20 naturally occurring, genetically encoded amino acids. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments of fibronectin and constitute one type of variant as described herein. Other variants include fragments of fibronectin in which a naturally occurring side chain of an amino acid residue (in either the L- or D-form) is replaced with a non-naturally occurring side chain.

In another aspect, the invention features polypeptides that include a sequence that is reversed with respect to the N- and C-termini of a sequence naturally found in a fibronectin polypeptide or a biologically active variant thereof. For example, the compositions of the invention can include polypeptides comprising the sequence TSTSTTTFDFD-FRTVEQHGYQQISILQ (SEQ ID NO: 9).

Any of the fragments of fibronectin in the present compositions can be one of a plurality present in a multimeric form (e.g., as a dimer). The multimeric form can also include one or more types of fragments (e.g., the two members of the dimer can be non-identical, e.g., in sequence or glycosylation pattern) and a backbone structure. Where two or more fragments are present, they may be identical or non-identical. A smaller structure, referred to as a linker, may also be present and may mediate attachment of the fragments to the backbone. Generally, the linker is smaller than the backbone. We have no reason to believe that the nature of the backbone structure is critical, and many different types of molecules may be used. One example of a linker structure is an oligolysine molecule having, for example, two or more lysine residues (e.g., 2, 3, 4, or more lysine residues). Two or more fragments of the invention (e.g., two three or four polypeptides) may be attached to lysine residues by, for example, peptide bonds. These fragments, having a polylysine linker, can be linked to a backbone structure. For example, the invention encompasses:

```
                                               (SEQ ID NO: 10)
    Backbone-KKKQLISIQQYGHQEVTRFDFTTTSTST
    and (SEQ ID NO: 11)
    QLISIQQYGHQEVTRFDFTTTSTSTKKK-Backbone.
```

A backbone structure, for example, one including an oligolysine molecule (e.g., as a linker), may be linear or branched. A multimeric peptide of the invention on a branched backbone molecule may be referred to herein as a "dendrimeric" peptide.

A fragment of fibronectin, including the variant forms described herein, can further include a heterologous polypeptide (i.e., a polypeptide having a sequence that does not appear in a fibronectin). The heterologous polypeptide can be a polypeptide that increases the circulating half-life of the fragment of fibronectin to which it is attached (e.g., fused, as in a fusion protein). The heterologous polypeptide can be an albumin (e.g., a human serum albumin or a portion thereof) or a portion of an immunoglobulin (e.g., the Fc region of an IgG).

The fragments of fibronectin can be contained within physiologically acceptable compositions or they may be contained within compositions that are not suitable for administration to a living being (e.g., concentrated stocks or frozen or lyophilized compositions). The physiologically acceptable compositions can be pharmaceutical compositions, and methods of treating patients are described further below. The physiologically acceptable compositions can also be non-pharmaceutical compositions or pharmaceutical compositions that can be dispensed without a physician's prescription. For example, they can be sold "over the counter" for cosmetic purposes (e.g., to reduce the risk of damage to the skin or to minimize or repair damage to the skin). For example, the fragments of fibronectin and compositions that include them can be incorporated in topical formulations sold as cosmetics, moisturizers and the like, sunscreens, shampoos or conditioners, soaps or other foaming cleansers, or lip balm.

The invention also encompasses nucleic acid molecules that encode the fragments of fibronectin described herein or the GFs that may be present in complexes with the FN fragments. Specific nucleic acid molecules, vectors (e.g., plasmid vectors), and host cells containing them are described further below, as are physiologically acceptable compositions containing them.

Other compositions of the present invention are tissue engineered products that include a fragment of a fibronectin or a biologically active variant thereof. As in other compositions, the fragment or the variant thereof can bind a polypeptide growth factor (as described above and further below), which factor may subsequently retain biological activity and may be administered to a patient.

More specifically, the tissue engineered product can be an artificial (or engineered) extracellular matrix (ECM). In addition to the fragment of fibronectin (or to a combination of such fragments), the tissue engineered product (e.g., the engineered ECM) can include a biocompatible polymer (e.g., hyaluronan (HA), a glycosaminoglycan (GAG), fibrinogen, laminin, or collagen). Silk, chitan and chitosan are also useful. The biocompatible polymer can be a biodegradable polymer, many of which are known in the art. For example, the biodegradable polymer can be a poly(lactide), a poly(glycolide), a poly(lactide-coglycolide), a poly(lactic acid), a poly(glycolic acid), a poly(lactic acid-co-glycolic acid), a poly(caprolactone), a polycarbonate, a polyesteramide, a polyanhydride, a poly(amino acid), a poly(ortho ester), a polycyanoacrylate, a polyamide, a polyacetal, a poly(ether ester), a copolymer of poly(ethylene glycol) and a poly(ortho ester), a poly(dioxanone), a poly(alkylene alkylate)s, a biodegradable polyurethane, or any blend or copolymer thereof. Other useful polymers include an alginate polymer and a carboxy-vinyl polymer (e.g., a polymer including at least 90% acrylic acid monomers and about 0.1% to about 5.0% of a difunctional crosslinking agent).

Other compositions of the present invention comprise a solid support that is associated with (e.g., bound to or impregnated with) one or more of the fragments of fibronectin, or the biologically active variants thereof, described herein. The fragment of fibronectin, or the biologically active variant thereof, can be bound to an active growth factor, including any of those described above. For example, the solid support can be a material within a bandage or dressing for wounds (e.g., an adsorbent material optionally attached to an adhesive strip). The solid support can also be a piece of tissue culture ware (e.g., a tissue culture plate, dish, flask, or the like), a bioreactor matrix, or a column, bead, or chip.

The methods of the invention include methods for treating a patient who has cancer. These methods can be carried out by, for example, administering to the patient a therapeutically effective amount of a pharmaceutical composition comprising a fragment of fibronectin, or a biologically active variant thereof, as described herein. The methods can optionally include a step of identifying a patient in need of treatment, and that patient can have a cancer associated with overexpression of a growth factor (e.g., overexpression of TGFβ1, TGFβ2, PDGF-BB, bFGF, FGF-7, VEGF-A or NGF. In addition to administration of a compositions described herein, the patient can receive a second type of treatment for cancer. That is, the present compositions can be used in conjunction with existing chemotherapies, radiation therapy, surgery, or any other cancer treatment.

Other methods of the invention are methods for promoting wound healing. These methods include a step of administering to a patient a therapeutically effective amount of a pharmaceutical composition comprising a fragment of fibronectin, or a biologically active variant thereof, as described herein. The fragment of fibronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, nerve or muscle; patients who are suffering from a traumatic laceration or tissue loss of the skin, mucosa, underlying connective tissue, fascia, nerve or muscle; and patients who are suffering from a burn or ulceration of the skin, mucosa, underlying connective tissue, fascia, nerve or muscle.

Suitable formulations are described further below and, generally, take the form of a solution, ointment or salve. The fragments of fibronectin, whether or not complexed with a growth factor, can also be administered by way of their inclusion in an engineered ECM, a bandage, dressing, compress, or the like.

By other methods of the invention, one can localize an endogenous growth factor to a tissue of a patient. These methods can be carried out by administering, to the patient, a therapeutically effective amount of a composition that includes a fragment of fibronectin, or a biologically active variant thereof, as described herein. As in the more specific treatment methods described above, these compositions can be administered by way of topical application of a pharmaceutical composition, an engineered ECM, or a solid support. These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureters, bladder or urethra dysfunction; an injury or loss to cartilage, synovium, menicus, ligament, tendon or nucleus pulposis or a disorder resulting in cartilage, synovium, menicus, ligament, tendon or nucleus pulposis dysfunction; an injury or loss to lips, tongue or gums or a disorder resulting in lip, tongue and gum dysfunction; an injury or loss to the subcutaneous tissue or a disorder resulting in subcutaneous tissue dysfunction.

In another aspect, the invention features methods for promoting the isolation, proliferation and/or differentiation of stem cells. The methods can be carried out with various compositions, including fragments of fibronectin per se as well as complexes containing such fragments bound to growth factors and the tissue-engineered solid-support products described herein. Similarly, one can promote the delivery of stem cells by administering to a patient a therapeutically effective amount of a composition that includes stem cells and a fragment of fibronectin as described herein (in its various forms, including forms in which the fragment of fibronectin is associated with a solid support or contained within a tissue engineered product). More generally, the methods of the invention include methods for promoting the isolation, proliferation, and delivery of cells. As noted, these cells can be stem cells or can be differentiating into, or differentiated into, epithelial cells, fibroblasts, myocytes, neural cells, endothelial cells, chondrocytes, hematopoietic cells or lymphocytes. The cells can be genetically engineered or simply isolated from a patient or a cell or tissue culture.

In another aspect, the invention features methods of screening for candidate inhibitors of growth factor-growth factor binding peptide complexes. The screening methods can be carried out by, for example: (a) providing (i) inducible cells, (ii) a tissue-engineered product or solid support comprising one or more fragments of fibronectin or biologically active variants thereof, (the fragments being, as described herein, capable of binding growth factors), (iii) one or more candidate inhibitors, and (iv) one or more growth factors; (b) contacting the cells in vitro with the tissue-engineered product or solid support; and (c) measuring the extent of cell function of the substrate.

The invention can also be described in terms of "use", in which case it encompasses "use" of the compositions described herein, including FN fragments, complexes containing these fragments and a bound GF, nucleic acids encoding the present FN fragments, expression vectors, host cells, and tissue engineered products for the treatment of cancer or for the preparation of a medicament for the treatment of cancer.

The invention further encompasses "use" of the compositions described herein, including FN fragments, complexes containing these fragments and a bound GF, nucleic acids encoding the present FN fragments, expression vectors, host cells, and tissue engineered products for promoting wound healing or for the preparation of a medicament for the promotion of wound healing.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 3 is an illustration of a method for synthesizing an ECM.

FIG. 4 is a representation of a plasma fibronectin polypeptide sequence (SEQ ID NO: 1).

DETAILED DESCRIPTION

Figure 1:
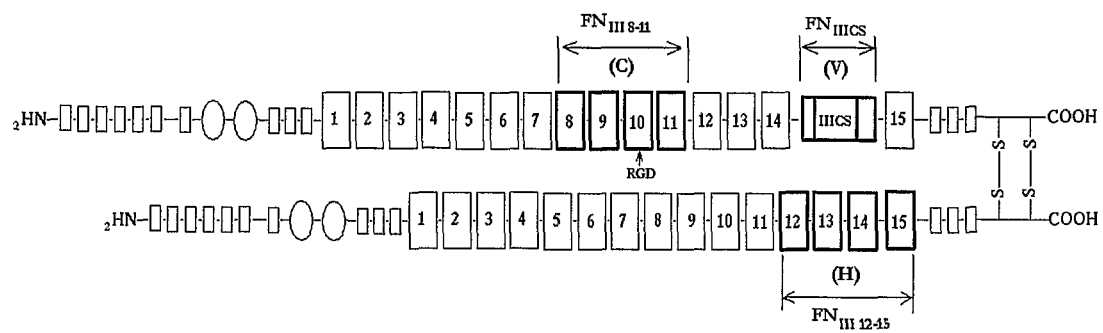
FIG. 1 is a diagram of human plasma fibronectin.
Figure 2:
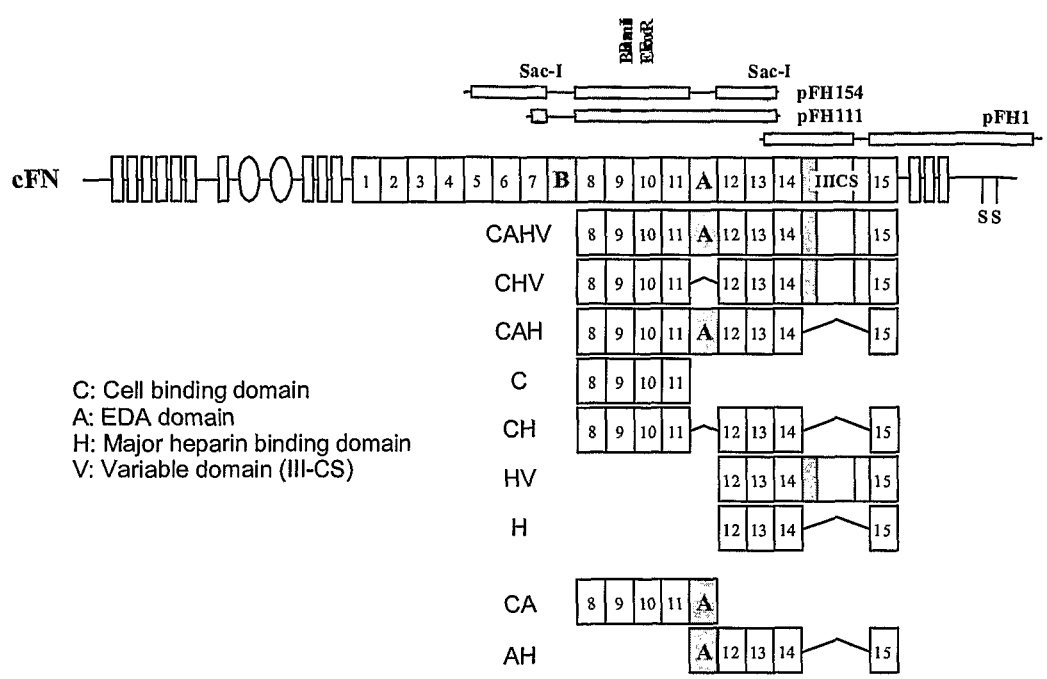
FIG. 2 is a diagram of cellular fibronectin (cFn). Various domains are illustrated.

Fibronectin is a multi-domain and multifunctional cell adhesion protein found in blood and various extracellular matrices. Fibronectin molecules consist of several functional domains, including: two heparin binding domains, Hep I and Hep II; two fibrin binding domains, Fib I and Fib II; a collagen or gelatin binding domain; an RGD cell-binding domain; and a variably spliced domain. Each functional domain is composed of highly homologous FN molecular domains: the type 1 repeats (FNI), type 2 repeats (FNII), and type 3 repeats (FNIII).

As detailed below, we have found, inter alia, that specific fragments of fibronectin can bind various growth factors (e.g., TGF-$\beta$1, TGF-$\beta$2, bFGF, FGF-7, PDGF-BB, VEGF-A, or NGF), and the bound growth factors can retain a biological activity. The present invention features compositions that include such fragments of fibronectin, with or without bound growth factors in the represented families (i.e., in the TGF, FGF, PDGF, VEGF, and NGF families), in various formulations and configurations. For example, the FN fragments, or FN fragment/GF-containing complexes can be incorporated into engineered three-dimensional extracellular matrices (which we may abbreviate herein as engECM or refer to as synthetic matrices), and these can include any of, or any combination of, the fibronectin fragments described herein (e.g., a FN polypeptide conforming to any of Formulas I, II, or III) or biologically active variants thereof. The growth factor(s) incorporated can be, for example, TGF-$\beta$1, TGF-$\beta$2, bFGF, FGF-7, PDGF-BB, VEGF-A, or NGF; any combination or sub-combination thereof; or another specific growth factor in the same family as those listed. The growth factors can be exogenously added to the FN fragment-containing formulation (e.g., a FN fragment-containing matrix), or the formulation (e.g., the matrix) can be generated without growth factors. In the latter case, when placed in the vicinity of an endogenous supply of growth factors, the growth factors can be recruited by the matrix. The matrix can also recruit cells and induce them to differentiate, produce tissue or proliferate (presumably by virtue of the inclusion or recruitment of growth factors, although the invention is not limited to compositions that function by any particular mechanism).

The matrix can include any type of hydrogel (e.g., an intramolecularly crosslinked hydrogel) and can include any of the materials typically included in hydrogels (e.g., hyaluronan). The hydrogel can include a biopolymer, and examples of suitable biopolymers are: proteins (e.g., collagen), protein-containing macromolecules (e.g., proteoglycans), silk (e.g., a derivatized silk), chitan and chitosan.

In one embodiment, the engineered extracellular matrix is composed of three fibronectin functional domains (FNfds) or biologically active variants or portions thereof: FNIII$_{8-11}$ (C), FNIII$_{12-15}$ (H) and FNIII$_{12-V15}$ (HV), which can be constructed recombinantly as arrayed on a natural FN heterodimer and incorporated into a hydrogel (e.g., tethered to an intramolecularly crosslinked hyaluronan (HA) hydrogel). The isolated domains useful within the present engineered matrices (e.g., $FNIII_{8-11}$ (C), $FNIII_{12-15}$ (H) and $FNIII_{12-V15}$ (HV)) are within the scope of the invention, and these domains can be formulated and modified as described herein for FN fragments, such as those conforming to any of formulas I, II, or III.

For preparation of pharmaceutical compositions containing the present fibronectin fragments and/or growth factors for prophylactic and/or therapeutic treatments, the active ingredients (e.g., the FN fragment alone or the FN fragment bound to GF(s)) can be incorporated alone or in combination with other active agents into compositions suitable for administration to a patient. The formulations can be made using methods routine in the art and particular guidance may be provided by prior formulations of protein-based therapeutics. The compositions will be physiologically acceptable (i.e., substantially non-toxic) and may be formulated as prescription medications or over-the-counter products. Pharmaceuticals or pharmaceutically acceptable compositions contain compounds (e.g., polypeptides, other materials (e.g., diluents), and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Nucleic acid molecules that encode the FN fragments described herein can also be formulated for administration. Such compositions commonly include a pharmaceutically acceptable carrier, and carriers are contemplated in the present formulations. Any conventional media or agent compatible with the active ingredients can be used in the present compositions. While formulations and methods of use are described further below, we note here that application to human patients is intended, as is application to animals (e.g., domesticated, farm, or show animals). The invention extends to non-physiologically acceptable compositions in that it extends to preparatory compositions and compositions suitable for storage (e.g., concentrated stocks and frozen or lyophilized preparations).

While specific FN fragments are described herein, the present compositions encompass those that include FN fragments of any length less than a full-length, naturally occurring fibronectin. For example, a FN fragment can lack one or more domains of fibronectin, provided that the sequence of the first fibronectin type III repeat domain, the thirteenth fibronectin type III repeat domain, and the III CS domain are present.

Fibronectin fragments featured herein can be described in a variety of ways and with respect to various features. With respect to length, the featured fragments can have about, or less than about, 500 (e.g., 510, 505, 501, or no more than 498, 488, 478, 468, 458, 448, 438, or 428), 400 (e.g., 410, 405, 401, or no more than 398, 388, 378, 368, 358, 348, 338, or 328), 300 (e.g., 310, 305, 301, or no more than 298, 288, 278, 268, 258, 248, 238, or 228), 200 (e.g., 210, 205, 201, or about or no more than 198, 188, 178, 168, 158, 148, 138, or 128), 100, 75, 50, 45, 40, 35, 30, 28, 27, 26, or 25 amino acid residues. For example, the fragment can include no more than 25 or 26 amino acid residues (e.g., no more than 26 amino acid residues that are identical to 26 contiguous amino acid residues found in a naturally occurring fibronectin protein).

With respect to length, the featured fragments can constitute about or no more than about 1-2%, 2-5%, 5-10%, or 10-25% of the amino acid sequence of a naturally occurring FN (e.g., as shown in FIG. 4). However, larger fragments may have GF-binding abilities and may therefore be useful as well.

With respect to sequence, the featured fragments of fibronectin can have a sequence that corresponds to or that is normally found within the region designated $FNIII_1$, $FNIII_2$, $FNIII_{12-14}$, $FNIII_{12-V15}$ (HV) or IIICS. The portions may be as short as 3-10 amino acid residues (e.g., 4, 5, 6, 7, or 8 contiguous residues).

More specifically, and in accordance with a consensus sequence based on some of the useful fragments of FN we discovered, the compositions of the present invention can include a fragment of fibronectin or a biologically active variant thereof that has an amino acid sequence conforming to Formula I:

$Xaa_1$-$Xaa_2$-$Xaa_3$-$Xaa_4$-$Xaa_5$-$Xaa_6$-$Xaa_7$-$Xaa_8$-$Xaa_9$-

$Xaa_{10}$-$Xaa_{11}$-$Xaa_{12}$-$Xaa_{13}$-$Xaa_{14}$-$Xaa_{15}$-$Xaa_{16}$-$Xaa_{17}$-

$Xaa_{18}$-$Xaa_{19}$ (Formula I)

In Formula I, $Xaa_1$ can be Gln or Asn (e.g., Gln); $Xaa_2$ can be any one or two amino acid residues (e.g., Pro, Leu-Ile, or Gly); $Xaa_3$ can be Ser or Thr (e.g., Ser); $Xaa_4$ can be absent or any single amino acid residue (e.g., $Xaa_4$ can be absent, His, or Val); $Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four or five amino acid residues (e.g., Leu-Arg-Trp-Arg (SEQ ID NO: 17)); $Xaa_{11}$ can be absent or any single amino acid residue (e.g., $Xaa_{11}$ can be absent or Pro); $Xaa_{12}$ can be Lys or Arg (e.g., Lys); $Xaa_{13}$ can be any one or two amino acid residues (e.g., Asn-Ser); $Xaa_{14}$ can be any one or two amino acid residues (e.g., Val-Gly); $Xaa_{15}$ can be Arg or Thr (e.g., Arg); $Xaa_{16}$ can be any one or two amino acid residues (e.g., Trp); $Xaa_{17}$ can be Lys, Gln, Thr, or Ser (e.g., Lys); $Xaa_{18}$ can be any two amino acid residues (e.g., Glu-Ala); and $Xaa_{19}$ can be Thr. In certain embodiments, certain provisos may apply. For example, the fragment of fibronectin, where identical to a portion of a naturally occurring fibronectin, may not be WNAPQPSHISKYILRWRPKNSVGRWKEATIPGHLNSY-TIKGLKPGVVYEGQLISIQ QYGHQEVTRFD-FTTTSTST (SEQ ID NO: 2) or may not be more than at least or about 40%, 50%, or 60% of this sequence (i.e., of SEQ ID NO: 2).

Specific fragments are described elsewhere herein and include those designated as peptides 1-4, 1A, and 1B. The specific sequences described herein are derived from a human plasma fibronectin. In addition, one can use corresponding sequences (e.g., fragments having a corresponding sequence from any fibronectin isoform of any species).

In other embodiments, the fragment of fibronectin used in one or more of the various compositions described herein, or biologically active variants thereof, can have, or can include, an amino acid sequence conforming to Formula II:

$Xaa_1$-$Xaa_2$-$Xaa_3$-$Xaa_4$-$Xaa_5$-$Xaa_6$-$Xaa_7$-$Xaa_8$-$Xaa_9$-$Xaa_{10}$-$Xaa_{11}$-$Xaa_{12}$ (Formula II).

In Formula II, $Xaa_1$ can be Gln or Asn (e.g., Gln); $Xaa_2$ can be any amino acid residue (e.g., Pro); $Xaa_3$ can be Ser or Thr (e.g., Ser); $Xaa_4$ can be any amino acid residue (e.g., His);

$Xaa_5$ can be Ile or Gly (e.g., Ile); $Xaa_6$ can be Ser or Gln (e.g., Ser); $Xaa_7$ can be Lys, Arg or Gln (e.g., Lys); $Xaa_8$ can be Tyr, Thr, or Met (e.g., Tyr); $Xaa_9$ can be Ile or Gly (e.g., Ile); $Xaa_{10}$ can be any four amino acid residues (e.g., Leu-Arg-Trp-Arg (SEQ ID NO: 17)); $Xaa_{11}$ can be any amino acid residue (e.g., Pro); and $Xaa_{12}$ can be Lys or Arg (e.g., Lys). For example, the compositions of the invention can include a fragment of fibronectin that has, or that includes, the sequence QPSHIS-KYILRWRPK (SEQ ID NO: 7).

In other embodiments, the fragment of fibronectin used in one or more of the various compositions described herein, or biologically active variants thereof, can have, or can include, an amino acid sequence conforming to Formula III:

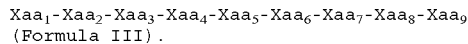
(Formula III).

In Formula III, $Xaa_1$ can be Ile or Gly (e.g., Ile); $Xaa_2$ can be any four or five amino acid residues and $Xaa_3$ can be absent or any single amino acid residue (e.g., $Xaa_2$ can be Leu-Arg-Trp-Arg-Pro and $Xaa_3$ can be absent or $Xaa_2$ can be Leu-Arg-Trp-Arg (SEQ ID NO: 17) and $Xaa_3$ can be Pro); $Xaa_4$ can be Lys or Arg (e.g., Lys); $Xaa_5$ can be any one or two amino acid residues (e.g., Asn-Ser); $Xaa_6$ can be any one or two amino acid residues (e.g., Val-Gly); $Xaa_7$ can be Arg or Thr (e.g., Arg); $Xaa_8$ can be any one or two amino acid residues (e.g., Trp); and $Xaa_9$ can be Lys, Gln, Thr, or Ser (e.g., Lys). For example, the compositions of the invention can include a fragment of fibronectin that has, or that includes, the sequence ILRWRPKNSVGRWK (SEQ ID NO: 8).

With respect to function, the featured fragments can bind a polypeptide growth factor with an affinity of about or at least about $1\times10^{-6}$-$1\times10^{-7}$ (e.g., about or at least about $5\times10^{-7}$; $1\times10^{-8}$; $5\times10^{-8}$; $1\times10^{-9}$; or $5\times10^{-9}$). In addition to GF-binding, the featured fragments can exhibit a certain degree of identity or homology to a corresponding wild type fragment of fibronectin. The extent of identity may be described not only in reference to the current polypeptides, but also in reference to the nucleic acid molecules that encode them. Biologically active variants of a fragment of fibronectin may differ from the wild type fragment by virtue of having one or more substitutions, additions or deletions of one or more amino acid residues. The substitutions can be conservative or non-conservative substitutions, and the amino acid side chains may also be modified.

Where a conservative amino acid substitution is made, the substitution can be of one amino acid residue for another in any of the following groups: arginine, histidine, and lysine; aspartic acid and glutamic acid; alanine, leucine, isoleucine and valine; and phenylalanine, tryptophan and tyrosine. The amino acid residues listed here are naturally occurring. Non-naturally occurring amino acid residues of like kind may also be substituted. For example, a negatively charged non-naturally occurring amino acid residue may be substituted for a negatively charged naturally occurring amino acid residue; a hydrophobic aromatic non-naturally occurring amino acid residue may be substituted for a hydrophobic aromatic naturally occurring amino acid residue; and so forth.

The degree of identity can vary and can be determined by methods well established in the art. "Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be referred to as homologous at that position. A percentage of homology or identity between sequences is a function of the number of matching or homologous positions shared by the sequences. A biologically active variant of a polypeptide described herein can have at least or about 25%, 50%, 65%, 75%, 80%, 85%, 90%, 95%, 96%, 97%, 98%, or 99% identity or homology to a corresponding naturally occurring polypeptide (e.g., a FN fragment). The nucleic acids encoding the biologically active variant polypeptides can be similarly described as having at least or about 25%, 50%, 65%, 75%, 80%, 85%, 90%, 95%, 96%, 97%, 98%, or 99% identity to a corresponding naturally occurring nucleic acid sequence. Those of ordinary skill in the art will readily recognize degenerate variants of nucleic acid sequences, and such variants can be used for the purposes described herein.

FN fragments and biologically active variants thereof can be modified in numerous ways. For example, agents, including additional amino acid residues, other substituents, and protecting groups can be added to either the amino terminus, the carboxy terminus, or both. The modification can be made for the purpose of altering the fragments' form or altering the way the fragments bind to or interact with one another, with non-identical fragments, or with other polypeptides. For example, the fragments can be modified to include cysteine residues or other sulphur-containing residues or agents that can participate in disulphide bond formation. For example, one can add at least two cysteine residues, one or both of which are, optionally, at the C-terminal or N-terminal of the fragment.

The fragments can be cyclized by formation of a disulfide bond between cysteine residues (or, more generally, between two of the at least two cysteine residues present in the polypeptide (e.g., at the terminal regions)). While the peptides of the present invention may be linear or cyclic, cyclic peptides generally have an advantage over linear peptides in that their cyclic structure is more rigid and hence their biological activity may be higher than that of the corresponding linear peptide (see, generally, Camarero and Muir, *J. Am. Chem. Soc.* 121:5597-5598, 1999).

Strategies for the preparation of circular polypeptides from linear precursors have been described and can be employed with the present FN fragments. For example, a chemical cross-linking approach can be used to prepare a backbone cyclized version of the peptide (Goldenburg and Creighton, *J. Mol. Biol.*, 165:407-413, 1983). Other approaches include chemical intramolecular ligation methods (see, e.g., Camarero et al., *Angew. Chem. Int. Ed.*, 37:347-349, 1998; Tam and Lu, *Prot. Sci.*, 7:1583-1592, 1998; Camarero and Muir, *Chem. Commun.*, 1997:1369-1370, 1997; and Zhang and Tam, *J. Am. Chem. Soc.* 119:2363-2370, 1997) and enzymatic intramolecular ligation methods (Jackson et al., *J. Am. Chem. Soc.*, 117:819-820, 1995), which allow linear synthetic peptides to be efficiently cyclized under aqueous conditions. See also U.S. Pat. No. 7,105,341.

Alternatively, or in addition, the fragment can further include a substituent at the amino-terminus or carboxy-terminus. The substituent can be an acyl group or a substituted or unsubstituted amine group (e.g., the substituent at the N-terminus can be an acyl group and the C-terminus can be amidated with a substituted or unsubstituted amine group (e.g., an amino group having one, two, or three substituents, which may be the same or different)). The amine group can be a lower alkyl (e.g., an alkyl having 1-4 carbons), alkenyl, alkynyl, or haloalkyl group. The acyl group can be a lower acyl group (e.g., an acyl group having up to four carbon atoms), especially an acetyl group.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. "Alkynyl" refers to an alkyl group having one or more triple carbon-carbon bonds. Example alkynyl groups include ethynyl, propynyl, and the like. "Haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As noted, the fragments can vary in length and can be or can include contiguous amino acid residues that naturally occur in fibronectin or that vary to a certain degree from a naturally occurring fibronectin sequence (but retain sufficient activity to be useful). Where the fragments include, at their N-terminus or C-terminus (or both), amino acid residues that are not naturally found in fibronectin, the additional sequence(s) can be about 200 amino acid residues long, and these residues can be divided evenly or unevenly between the N- and C-termini. For example, both the N- and C-termini can include about 10, 20, 30, 40, 50, 60, 70, 80, 90, or 100 amino acid residues. Alternatively, one terminus can include about 10, 20, 30, 40, 50, 60, 70, 80, 90, 100, 110, 120, 130, 140, 150, 160, 170, 180, 190, or 200 residues, and one terminus can include none (e.g., it can terminate in an amino acid sequence identical to a naturally occurring fibronectin sequence).

More specifically, the N- or C-termini can include 1 to about 100 (e.g., 1, 2, 3, 4, 5, 6, 7, 8, 9, 10, 15, 20, 25, 30, 40, 50, 60, 70, 80, 90, or 100) amino acid residues that are positively charged (e.g., basic amino acid residues such as arginine, histidine, and/or lysine residues); 1 to about 100 amino acid residues that are negatively charged (e.g., acidic amino acid residues such as aspartic acid or glutamic acid residues); 1 to about 100 glycine residues; 1 to about 100 hydrophobic amino acid residues (e.g., hydrophobic aliphatic residues such as alanine, leucine, isoleucine or valine or hydrophobic aromatic residues such as phenylalanine, tryptophan or tyrosine); or 1 to about 100 (e.g., 1-4) cysteine residues.

The fragments of fibronectin, including the modified fragments described above, can be protease resistant and can include one or more types of protecting groups such as an acyl group, an amide group, a benzyl or benzoyl group, or a polyethylene glycol. More specifically, a fragment of fibronectin, including the modified fragments described above, can be N-terminally acetylated and/or C-terminally amidated.

Where non-naturally occurring or modified amino acid residues are included they can be selected from the following or many others available in the art: 4-hydroxyproline, gamma-carboxyglutamic acid, o-phosphoserine, o-phosphotyrosine, or delta-hydroxylysine. Other examples include naphthylalanine, which can be substituted for trytophan to facilitate synthesis, L-hydroxypropyl, L-3,4-dihydroxyphenylalanyl, alpha-amino acids such as L-alpha-hydroxylysyl and D-alpha-methylalanyl, L-alpha-methylalanyl, beta-amino acids, and isoquinolyl. Fragments having non-naturally occurring amino acid residues may be referred to as synthetic fragments of fibronectin and constitute one type of variant as described herein. Other variants include fragments of fibronectin in which a naturally occurring side chain of an amino acid residue (in either the L- or D-form) is replaced with a non-naturally occurring side chain.

In one embodiment, the FN fragments can have three extra amino acids (MetGlySer) at either terminus (or both) (e.g., at the N-terminus) and seven to eight extra amino acids (ThrSerHisHisHisHisHisHisCys (SEQ ID NO: 12)) at either terminus (or both) (e.g., at the C-terminus).

For guidance on FN fragment modification by reduction/alkylation and/or acylation, one can consult Tarr, *Methods of Protein Microcharacterization*, J. E. Silver ed., Humana Press, Clifton N.J. 155-194, 1986; for guidance on chemical coupling to an appropriate carrier, one can consult Mishell and Shiigi, eds, *Selected Methods in Cellular Immunology*, WH Freeman, San Francisco, Calif. (1980) and U.S. Pat. No. 4,939,239; and for guidance on mild formalin treatment, one can consult Marsh, *Int. Arch. of Allergy and Appl. Immunol.*, 41:199-215, 1971.

Any of the fragments of fibronectin in the featured compositions can be one of a plurality present in a multimeric form (e.g., a dimer). The multimeric form can also include one or more types of fragments and a backbone structure. Where two or more fragments are present, they may be identical or non-identical. A smaller structure, referred to as a linker, may also be present and may mediate attachment of the fragments to the backbone. Generally, the linker is smaller than the backbone. The nature of the backbone structure is not critical, and many different types of molecules may be used. One example of a linker structure is an oligolysine molecule having, for example, two or more lysine residues (e.g., 2, 3, 4, or more lysine residues). Two or more fragments of the invention (e.g., two three or four polypeptides) may be attached to lysine residues by, for example, peptide bonds. These fragments, having a polylysine linker, can be linked to a backbone structure. For example, the invention encompasses:

```
                                               (SEQ ID NO: 10)
Backbone-KKKQLISIQQYGHQEVTRFDFTTTSTST
and (SEQ ID NO: 11)
QLISIQQYGHQEVTRFDFTTTSTSTKKK-Backbone.
```

A backbone structure, for example, an oligolysine molecule, may be linear or branched. A multimeric peptide of the invention on a branched backbone molecule may be referred to herein as a "dendrimeric" peptide.

A fragment of fibronectin, including the variant forms described herein, can further include a heterologous polypeptide (i.e., a polypeptide having a sequence that does not appear in a fibronectin). The heterologous polypeptide can be a polypeptide that increases the circulating half-life of the fragment of fibronectin to which it is attached (e.g., fused, as in a fusion protein). The heterologous polypeptide can be an albumin (e.g., a human serum albumin or a portion thereof) or a portion of an immunoglobulin (e.g., the Fc region of an IgG).

Polypeptide growth factors that can be bound by the FN fragments described herein can be within the transforming growth factor (TGF) family (e.g., TGF-β1 or TGF-β2), within the fibroblast growth factor (FGF) family (e.g. bFGF or FGF-7), within the platelet-derived growth factor (PDGF) family (e.g., PDGF-BB), within the vascular endothelial growth factor (VEGF) family (e.g., VEGF-A), or within the nerve growth factor (NGF) family.

To determine whether fibronectin fragments bind growth factors that have retained a biological activity, standard biological assays can be carried out. For example, as outlined in the Examples below, migratory responses to bound growth factors that usually stimulate migration can be carried out. For example, one can compare the effect of a bound and unbound growth factor on fibroblast migration or granulation tissue formation. Specifically, if a growth factor is a PDGF (e.g., PDGF-BB), migration of AHDF cells can be analyzed.

Compounds mimicking the necessary conformation of fibronectin fragments that bind growth factors are contemplated as within the scope of this invention. A variety of designs for such mimetics are possible. U.S. Pat. Nos. 5,192,746; 5,169,862; 5,539,085; 5,576,423; 5,051,448; and 5,559,103, all hereby incorporated by reference, describe multiple methods for creating such compounds.

Synthesis of non-peptide compounds that mimic peptide sequences is also known in the art (see, e.g., Eldred et al. (*J. Med. Chem.* 37:3882, 1994; Ku et al. (*J. Med. Chem.* 38:9, 1995). Such nonpeptide compounds that mimic fibronectin fragments that bind growth factors are specifically contemplated by the present invention.

The present invention also contemplates synthetic mimicking compounds that are multimeric by virtue of repeating the relevant fibronectin fragment sequence. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the (α-amino group of the component containing the activated carboxyl group can be blocked with a tertbutyloxycarbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

In one embodiment, the mimetics of the present invention are peptides having sequence homology to the herein-described fibronectin fragments (including, but not limited to, peptides in which L-amino acids are replaced by their D-isomers). One common methodology for evaluating sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant (Pearson and Lipman, *Proc. Natl. Acad. Sci.* (*USA*), 85:2444-2448, 1988; Lipman and Pearson, *Science,* 227:1435-1441, 1985).

More generally, the FN fragments described herein and the mimetics described above can be synthesized using any known methods, including tea-bag methodology or solid phase peptide synthesis procedures described by Merrifield et al. (*Biochemistry* 21:5020-5031, 1982), Houghten Wellings (*Proc. Natl. Acad. Sci.* (*USA*) 82:5131-5135, 1985); Atherton, *Methods in Enzymology* 289:44-66, 1997, or Guy and Fields, *Methods in Enzymology* 289:67-83, 1997, or using a commercially available automated synthesizer.

A present pharmaceutical composition is formulated to be compatible with its intended route of administration, for example, oral or parenteral (e.g., intravenous, intradermal, subcutaneous, intraperitoneal, intramuscular, by inhalation, transdermal (topical), and transmucosal administration). Given the ability of the present FN fragments, and GF-containing complexes bearing this fragments, to facilitate wound healing, topical formulations are particularly envisioned. Solutions or suspensions used for parenteral administration can include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The composition can be aliquoted or packaged in ampules, disposable syringes, single or multiple dose vials made of glass or plastic, bottles, and the like, and such packaged forms, along with instructions for use, are within the scope of the present invention. Preferably, the compositions are sterile at a medically acceptable level in view of the intended route of administration.

Pharmaceutical compositions adapted for injection include, for example, sterile aqueous solutions (where water soluble) or dispersions and sterile powders for the extemporaneous preparation of sterile injectable solutions or dispersion. For intravenous administration, suitable carriers include, for example, physiological saline, bacteriostatic water, Cremophor EL™ (BASF, Parsippany, N.J.) and phosphate buffered saline (PBS). In all cases, the compositions prepared for administration should be sterile and should be fluid or convertible to a fluid at least sufficient for easy syringability. The composition and/or nucleic acid constructs should be stable under the conditions of manufacture and storage and should be preserved against the contaminating action of microorganisms such as bacteria and fungi. Preservatives against microorganisms can include various antibacterial and antifungal agents, for example, parabens, chlorobutanol, phenol, ascorbic acid, thimerosal, and the like.

The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersions and by the use of surfactants.

In many cases, it will be desirable for the composition to be isotonic to blood. This can be accomplished using various isotonic agents, for example, sugars, polyalcohols such as manitol, sorbitol, sodium chloride in the composition.

Delayed or extended absorption of the injectable compositions can be desirable and can be achieved by including in the composition an agent which delays absorption, for example, aluminum monostearate and gelatin, or by coating micro- or nano-particles of active agent in the composition with materials that delayed or extended release of components.

Sterile injectable solutions can be prepared, for example, by solubilizing or suspending the active compound in the required amount in an appropriate solvent with one or a combination of additional ingredients. Typically creation of such solution or suspension is followed by sterile filtration. Generally, dispersions are prepared by incorporating the active compound into a sterile vehicle which contains a basic dispersion medium and the other desired ingredients. In the case of sterile powders for the preparation of sterile injectable solutions, the preparation is dried, e.g., by vacuum drying and/or freeze-drying.

Compositions for oral administration typically include an inert or edible diluent or edible carrier. Such compositions can be formulated in various ways, e.g., in liquid, capsule, or tablet form. Pharmaceutically compatible binding agents, and/or adjuvant materials can be included as part of the composition. The tablets, pills, capsules, troches and the like can contain any one or more of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For inhalation administration (e.g., for application to cancerous cells within the nasal passages, nasopharynx, trachea or lungs or for application to wounded tissues (e.g., mucosa) in these regions), the present compositions are delivered in the form of a wet or dry aerosol spray, e.g., from a pressured container or dispenser which contains a suitable propellant, e.g., a gas such as carbon dioxide, or a nebulizer.

Systemic administration can also be by transmucosal or transdermal routes. For transmucosal or transdermal administration, penetrants appropriate to the barrier to be permeated are typically used in the formulation. A number of such penetrants are generally known in the art, and include, for example, for transmucosal administration, detergents, bile salts, and fusidic acid derivatives.

Transmucosal administration can be accomplished through the use of nasal sprays or suppositories (e.g., using conventional suppository bases such as cocoa butter and other glycerides). For transdermal administration, the active compounds are formulated into ointments, salves, gels, or creams as generally known in the art.

Such compositions can also be formulated with carriers that will protect the compositions against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. The materials can also be obtained commercially, e.g., from Alza Corporation and Nova Pharmaceuticals, Inc. Liposomal suspensions (including liposomes targeted to particular cells (e.g., targeted to infected cells) with monoclonal antibodies) can also be used to prepare pharmaceutical compositions. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of active compounds and pharmaceutical compositions can be determined by standard pharmaceutical procedures in cell cultures or experimental animals. For example, such procedures are routinely applied for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred.

The data obtained from the cell culture assays and animal studies (including those described in the examples, below) can be used in formulating a range of dosage for use in humans or other intended subject. The dosage of such compounds is usually selected to produce a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Thus, for example, a dose may be initially established in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography, or by other suitable analysis method adapted for the compound of interest.

As noted, peptides (e.g., synthetic or recombinantly produced peptides) with growth factor-binding activity can be incorporated into a tissue engineered product. FN domains that promote fibroblast migration can also be included. Preferably, the products are robust (i.e., relatively resistant to rapid degradation). They can be used, for example, in treating wounds, including acute or non-healing wounds (e.g., chronic ulcers). Patients amenable to treatment are described further below. Alternatively or in addition, growth factor-binding peptides can be tethered to a biocompatible polymer for delivery of one or more growth factors to a cell, tissue or organ in need of treatment.

We have developed an engineered ECM that is conductive and inductive of new tissue formation in porcine cutaneous wounds utilizing molecular domains C, H, and HV of the blood protein fibronectin (FN) tethered to an intramolecularly crosslinked hyaluronin (HA) hydrogel. Thus, in one implementation, the invention includes an engineered ECM that includes a fragment of a fibronectin (e.g., a plasma fibronectin) or a biologically active variant thereof. The fragment can be tethered to (e.g., covalently or non-covalently bound to) a hydrogel (e.g., an HA hydrogel) and can be a fragment that binds a polypeptide growth factor. The fragment can be tethered according to attachment methods discussed in U.S. Pat. Application 20050282747, the contents of which are incorporated herein in their entirety.

The naturally-occurring ECM is comprised of diverse constituents such as glycoproteins, proteoglycans, complex carbohydrates, and other molecules. Major functions of the ECM include, but are not limited to, providing structural support, tensile strength or cushioning; providing substrates and pathways for cell adhesion and cell migration; and regulating cellular differentiation and metabolic function. ECM proteins include, for example, collagens, elastin, fibronectin, laminin, proteoglycans, vitronectin, thrombospondin, tenascin (cytoactin), entactin (nidogen), osteonectin (SPARC), anchorin CII, chondronectin, link protein, osteocalcin, bone sialoprotein, osteopontin, epinectin, hyaluronectin, amyloid P component, fibrillin, merosin, s-laminin, undulin, epilligrin, and kalinin.

In addition to the fragment of fibronectin, the featured tissue engineered product (e.g., the engineered ECM) can biological and/or synthetic components. It can include a biocompatible polymer (e.g., hyaluronan (HA), a glycosaminoglycan (GAG), fibrinogen, laminin, or collagen). The biocompatible polymer can be a biodegradable polymer, many of which are known in the art. For example, the biodegradable polymer can be a poly(lactide), a poly(glycolide), a poly (lactide-coglycolide), a poly(lactic acid), a poly(glycolic acid), a poly(lactic acid-co-glycolic acid), a poly(caprolactone), a polycarbonate, a polyesteramide, a polyanhydride, a poly(amino acid), a poly(ortho ester), a polycyanoacrylate, a polyamide, a polyacetal, a poly(ether ester), a copolymer of poly(ethylene glycol) and a poly(ortho ester), a poly(dioxanone), a poly(alkylene alkylate)s, a biodegradable polyurethane, or any blend or copolymer thereof. Other useful polymers include an alginate polymer and a carboxy-vinyl polymer (e.g., a polymer including at least 90% acrylic acid monomers and about 0.1% to about 5.0% of a difunctional crosslinking agent).

A tissue engineered "smart" matrix that would be conductive and inductive of tissue cell repopulation of a wound site and the development of new tissue, respectively, should be composed of GFs in the context of an appropriate ECM that are required for optimal wound repair. In addition, FN GF-binding domain(s) may provide a useful tool for engineering many other GF localization (from endogenous or exogenous sources) and/or delivery systems for soft or hard tissue repair, augmentation and regeneration. Furthermore, molecularly engineered derivatives of the FN GF-binding domains might become strongly inhibitory of GF activity and thus useful for proliferative or fibrotic disorders such as cancer, pulmonary fibrosis, GI or GU stenosis, burn contractures and autoimmune generated sclerosis.

EngECM can be generated with or without growth factors, e.g., growth factors described herein. In the former case, the dosage of growth factors in the engECM can vary, e.g., as described below, 100 ng/ml (15 ng total per wound) of PDGF-BB added to 2:1 engineered ECM enhanced granulation formation at 4 days after injury and application of material. In the latter case, when placed in the vicinity of an endogenous supply of growth factors, the growth factors can be recruited by the matrix.

The invention further encompasses nucleic acid molecules, including DNA and RNA molecules, that encode the polypeptides described herein. For example, a nucleic acid molecule can encode the C, H, or HV domains or portions thereof for inclusion in engineered ECMs; $FNIII_{11-12}$ or a portion thereof; $FNIII_1$ or a portion thereof; $FNIII_2$ or a portion thereof; $FNIII_{12-V15}$ or a portion thereof; $FNIII_{12-15}$ or a portion thereof; $FNIII_{12-14}$ or a portion thereof; $FNIII_{12-13}$ or a portion thereof; $FNIII_{13-14}$ or a portion thereof; IIICS or a portion thereof.

The nucleic acid molecules can be formulated in physiologically acceptable compositions for administration.

The invention also features vectors that include the present nucleic acid constructs. Of particular benefit are expression vectors, especially those for expression in eukaryotic cells. Such vectors can, for example, be viral, plasmid, cosmid, or artificial chromosome (e.g., yeast artificial chromosome) vectors.

Typically, plasmids are circular, dsDNA elements that include one or more cloning sites for insertion of selected DNA sequences, e.g., coding sequences. Such plasmids may include a functional origin of replication and thus are replication competent, or may be replication defective.

In addition to plasmids, viral vectors (e.g., replication defective retroviruses, lentiviruses, adenoviruses and adeno-associated viruses) can also be advantageously used. A large number of such viral vectors have been developed having a broad variety of different properties. For example, such viral vectors may be replication defective retroviruses, adenoviruses and adeno-associated viruses. Techniques and procedures for producing recombinant retroviruses and for infecting cells in vitro or in vivo with such viruses are provided in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psi.Crip, psi.Cre, psi.2 and psi.Am.

The genome of adenovirus can be manipulated such that it encodes and expresses a nucleic acid construct, as described herein, but is inactivated in terms of its ability to replicate in a normal lytic viral life cycle. (see, e.g., Berkner et al., *BioTechniques* 6:616, 1988; Rosenfeld et al., *Science* 252:431-434, 1991; and Rosenfeld et al., *Cell* 68:143-155, 1992). Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (*Mol. Cell. Biol.* 5:3251-3260, 1985) can be used to express a transactivator fusion protein.

Other viral vector alternatives include lentiviral vectors. Such vectors and their preparation and use are described, for example, in U.S. Pat. Nos. 6,924,123; 6,863,884; 6,830,892; 6,818,209; 6,808,923; 6,799,657, all of which are incorporated herein in their entireties.

The vectors of the invention can advantageously include a fibronectin fragment described herein. Other elements included in the design of a particular expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The vectors described herein can be introduced into cells or tissues by any one of a variety of known methods within the art. Such methods are described for example in Sambrook et al., Molecular Cloning: A Laboratory Manual, Cold Spring Harbor Laboratory, N.Y.(1992), which is hereby incorporated by reference. See, also, Ausubel et al., Current Protocols in Molecular Biology, John Wiley and Sons, Baltimore, Md. (1989); Hitt et al., "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al., "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook," Ed. J. E. Celis. Academic Press. pp: 479-490, 1994, also hereby incorporated by reference. The methods include, for example, stable or transient transfection, lipofection, electroporation and infection with recombinant viral vectors. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (Molecular Cloning: A Laboratory Manual, 2nd Edition, Cold Spring Harbor Laboratory press (1989)), and other laboratory textbooks.

For plant cells, a Ti plasmid or viral vector is often used. For example, such plasmids and viral vectors can be used to transfect host plant cells via *Agrobacterium tumefaciens*-mediated transfection (for plant cells susceptible to *A. tumefaciens* infection), or can be directly inserted in cells, e.g., using microinjection, particle bombardment, or electroporation. In other methods, protoplasts can be made from plant cells and then transfected.

The number of host cells transformed with a nucleic acid constructs of the invention will depend, at least in part, upon the type of recombinant expression vector and the type of transfection technique used. Nucleic acid can be introduced into a host cell transiently, or for long-term expression. For long-term expression, the nucleic acid is stably integrated into the genome of the host cell or remains as a stable episomal element.

For integration of nucleic acid into host cell DNA, typically a gene is used that encodes a selectable marker (e.g., drug resistance) is introduced into the host cells along with the nucleic acid of interest. A variety of such selectable markers are commonly used, such as the drugs hygromycin and neomycin. Selectable markers can be introduced on a separate plasmid or other vector from the nucleic acid of interest or, are introduced on the same vector. Host cells transfected with a nucleic acid construct of the invention (e.g., a recombinant expression vector) and a gene for a selectable marker can be identified by selecting for cells using the selectable marker.

The present nucleic acid constructs can be introduced into eukaryotic cells growing in culture in vitro by conventional transfection techniques (e.g., calcium phosphate precipitation, DEAE-dextran transfection, electroporation, and other methods). Cells can also be transfected in vivo, for example by application of a delivery mechanism suitable for introduction of nucleic acid into cells in vivo, such as viral vectors (see e.g., Ferry, N et al. (1991) Proc. Natl. Acad. Sci. USA 88:8377-8381; and Kay, M. A. et al. (1992) Human Gene Therapy 3:641-647), adenoviral vectors (see e.g., Rosenfeld, M. A. (1992) Cell 68:143-155; and Herz, J. and Gerard, R. D. (1993) Proc. Natl. Acad. Sci. USA 90:2812-2816), receptor-mediated DNA uptake (see e.g., Wu, G. and Wu, C. H. (1988) J. Biol. Chem. 263:14621; Wilson et al. (1992) J. Biol. Chem. 267:963-967; and U.S. Pat. No. 5,166,320), direct injection of DNA (see e.g., Acsadi et al. (1991) Nature 332: 815-818; and Wolff et al. (1990) Science 247:1465-1468) or particle bombardment (see e.g., Cheng, L. et al. (1993) Proc. Natl. Acad. Sci. USA 90:4455-4459; and Zelenin, A. V. et al. (1993) FEBS Letters 315:29-32). Thus, in the present invention, cells can be transfected in vitro or ex vivo, and administered to a subject or, alternatively, cells can be directly modified in vivo.

Another aspect of the invention pertains to host cells into which a nucleic acid construct of the invention has been introduced, i.e., a "recombinant host cell." It is understood that the term "recombinant host cell" refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell, although eukaryotic cells are preferred. Exemplary eukaryotic cells include mammalian cells (such as Chinese hamster ovary cells (CHO) or COS cells). Other suitable host cells are known to those skilled in the art.

It is not intended that the present invention be limited by the particular nature of the therapeutic preparation, so long as the preparation comprises an appropriate fragment of fibronectin that binds a polypeptide growth factor. For example, such compositions can be provided together with physiologically tolerable liquid, gel or solid carriers, diluents, adjuvants and excipients.

These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Formulations can include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%.

The compositions are also prepared as injectables, either as liquid solutions or suspensions; solid forms suitable for solution in, or suspension in, liquid prior to injection may also be prepared.

The fibronectin fragments of the present invention are often mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

The invention features treating cancers that include various malignant and benign tumors such as malignant melanoma, malignant lymphoma, digestive cancers, lung cancer, esophageal cancer, stomach cancer, large bowel cancer, rectum cancer, colon cancer, ureteral tumor, gallbladder cancer, bile duct cancer, biliary tract cancer, breast cancer, liver cancer, pancreas cancer, testicular tumor, maxillary cancer, lingual cancer, lip cancer, mouth cancer, pharyngeal cancer, ovarian cancer, uterine cancer, prostate cancer, thyroid gland cancer, brain tumor, Kaposi's sarcoma, hemangioma, leukemia, polycythemia vera, neuroblastoma, retinoblastoma, myeloma, bladder tumor, sarcoma, osteosarcoma, myosarcoma, skin cancer, renal cancer, urinary cancer, childhood cancers, glioma and the like.

The present methods are particularly effective for tumor-suppression of growth factor-related cancers, for example, hyperproliferative cancers. Signaling pathways that mediate normal function of growth factors are often dysregulated in various cancers, which can lead to, for example, malignancy.

Growth factors that promote angiogenesis can also contribute to tumor growth and/or progression.

The featured methods can be carried out by, for example, administering to the patient a therapeutically effective amount of a pharmaceutical composition comprising a fragment of fibronectin, or a biologically active variant thereof, as described herein. The methods can optionally include a step of identifying a patient in need of treatment, and that patient can have a cancer associated with overexpression of a growth factor (e.g., overexpression of TGFβ1, TGFβ2, PDGF-BB, bFGF, FGF-7, VEGF-A or NGF. In addition to administration of a compositions described herein, the patient can receive a second type of treatment for cancer. That is, the present compositions can be used in conjunction with existing chemotherapies, radiation therapy, surgery, or any other cancer treatment.

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson in *Current Surgical Diagnosis & Treatment* (Way; Appleton & Lange), pp. 86-98, 1988).

The term "wound" refers broadly to injuries to the skin and subcutaneous tissue initiated in different ways (e.g., pressure sores from extended bed rest and wounds induced by trauma) and with varying characteristics and to injuries in or around the orifices of the body. Of course, wounds can also be made surgically or by disease (e.g. cancer). Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The present invention contemplates treating all wound types, including deep wounds and chronic wounds.

The phrases "promote wound healing," "enhance wound healing," and the like refer to either the induction of the formation of granulation tissue of wound contraction and/or the induction of epithelialization (i.e., the generation of new cells in the epithelium). Wound healing is conveniently measured by decreasing wound area. It is not intended that phrases such as "promote wound healing" or "enhance wound healing" require a quantitative comparison with controls. In the case of treatment of a chronic wound, it is sufficient that evidence of wound healing begin after treatment.

Many traumatic wounds and cancer extirpations must be left open to heal by secondary intention, and patients having such wounds and extirpations can be treated with the compositions described herein that promote wound healing. The incidence of chronic wounds, sometimes referred to as non-healing wounds, is rising due to events such as aging populations; an increase in age-related diseases in those populations; an increase in the incidence of AIDS; and an increase in radiation wounds secondary to cancer intervention. Patients who have chronic wounds, including those associated with the events just described, can be treated with the compositions described herein that promote wound healing.

The present compositions can be used either instead of or to supplement existing wound-care procedures such as skin grafting and tissue flaps, debridement, and the administration of anti-inflammatory, antibacterial and/or anti-pain medications. Patients amenable to treatment include those who have chronic dermal ulcerations, as can occur in association with diabetes. Diabetic ulcers, however, are just one part of the chronic wound picture. It is estimated that 5.5 million people in the United States have chronic, nonhealing wounds.

The methods of the invention include a step of administering to a patient a therapeutically effective amount of a pharmaceutical composition comprising a fragment of fibronectin, or a biologically active variant thereof, as described herein. The fragment of fibronectin, or the biologically active variant thereof, can be present in a complex with one or more growth factors. The methods can optionally include a step of identifying a patient in need of treatment. Such patients include patients who are suffering from a surgical extirpation or incision of the skin, mucosa, underlying connective tissue, fascia, nerve or muscle; patients who are suffering from a traumatic laceration or tissue loss of the skin, mucosa, underlying connective tissue, fascia, nerve or muscle; and patients who are suffering from a burn or ulceration of the skin, mucosa, underlying connective tissue, fascia, nerve or muscle.

Suitable formulations are described herein and, generally, take the form of a solution, ointment or salve. The fragments of fibronectin, whether or not complexed with a growth factor, can also be administered by way of their inclusion in an engineered ECM, a bandage, dressing, compress, or the like.

By other methods of the invention, one can localize an endogenous growth factor to a tissue of a patient. These methods can be carried out by administering, to the patient, a therapeutically effective amount of a composition that includes a fragment of fibronectin, or a biologically active variant thereof, as described herein. As in the more specific treatment methods described herein, these compositions can be administered by way of topical application of a pharmaceutical composition, an engineered ECM, or a solid support. These methods can be described as methods of delivering one or more growth factors to a patient. The methods can optionally include a step of identifying a patient in need of treatment. Such patients include patients who are suffering from an injury to a tissue, a loss of a tissue or a disorder resulting in tissue disfigurement or dysfunction. More specifically, the patient can be suffering from an injury or loss to the brain, spinal cord or nerves or a disorder resulting in brain, spinal cord or nerve dysfunction; an injury or loss to the heart or blood vessels or a disorder resulting in heart or blood vessel dysfunction; an injury or loss to the lung, nasopharyngeal tract, sinuses, trachea or airways or a disorder resulting in lung, nasopharyngeal tract, sinus, trachea or airway dysfunction; an injury or loss to the gastrointestinal tract, liver or pancreas or a disorder resulting in gastrointestinal tract, liver or pancreas dysfunction; an injury or loss to a kidney, ureters, bladder or urethra or a disorder resulting in kidney, ureters, bladder or urethra dysfunction; an injury or loss to cartilage, synovium, menicus, ligament, tendon or nucleus pulposis or a disorder resulting in cartilage, synovium, menicus, ligament, tendon or nucleus pulposis dysfunction; an injury or loss to lips, tongue or gums or a disorder resulting in lip, tongue and gum dysfunction; an injury or loss to the subcutaneous tissue or a disorder resulting in subcutaneous tissue dysfunction.

The invention also features methods for promoting the isolation, proliferation and/or differentiation of stem cells. The methods can be carried out with various compositions, including fragments of fibronectin per se as well as complexes containing such fragments bound to growth factors and the tissue-engineered solid-support products described herein. Similarly, one can promote the delivery of stem cells by administering to a patient a therapeutically effective amount of a composition that includes stem cells and a fragment of fibronectin as described herein (in its various forms, including forms in which the fragment of fibronectin is associated with a solid support or contained within a tissue engineered product). More generally, the methods of the invention include methods for promoting the isolation, proliferation, and delivery of cells. As noted, these cells can be stem cells or can be differentiating into, or differentiated into, epithelial cells, fibroblasts, myocytes, neural cells, endothelial cells, chondrocytes, hematopoietic cells or lymphocytes. The cells can be genetically engineered or simply isolated from a patient or a cell or tissue culture.

EXAMPLES

Fibronectin growth factor-binding domains are promiscuous and can tether active GF to the ECM or maintain or enhance GF activity in solution Data from our laboratory has demonstrated the binding of TGF-β1, PDGF-BB, VEGF-A, and FGF-2 with fibronectin (FN) and its functional domains as well as biological implications of these interactions. Briefly, radiolabeled GFs bound intact FN with the following KDs as judged by non linear regression: TGF-β1, KD=5.3× $10^{-8}$ M; PDGF-BB, KD=4.9×$10^{-}$M, FGF-2, KD=4.4×$10^{-8}$ M. As determined by plasmon resonance modulation, all GFs, except EGF, bound to the composite heparinII-binding and variably-spliced IIICS domains ($FNIII_{12-v15}$) with the following order of affinities: VEGF (KD=6.0×$10^{-10}$ M)>TGF-β1 (KD=2.5×$10^{-9}$ M)>PDGF-BB (KD=1.7×$10^{-8}$ M)>FGF-2 (KD=3.7×$10^{-8}$ M). Similar rank orders of affinities were observed with GF binding to the heparinII-binding domain ($FNIII_{12-15}$ and $FNIII_{12-14}$): PDGF-BB (KD=6.8×$10^{-8}$ M)≥TGF-β1 (KD=1.6×$10^{-8}$ M)>FGF-2 (KD=1.7×$10^{-7}$ M); TGF-β1 (KD=7.6×$10^{-9}$ M)>PDGF-BB (KD=5.5×$10^{-8}$ M), respectively. VEGF, TGF-β1, PDGF-BB and FGF-2 bound IIICS with similar affinities (KD~$10^{-7}$ M). EGF again failed to bind this functional domain and all others tested. None of the GFs detectably bound the amino-terminal end of FN ($FN_{70}$) nor the classic cell-binding domain containing RGD ($FNIII_{8-11}$). Although TGF-β1 and PDGF-BB bound the $FNIII_{1-11}$, VEGF and FGF-2 did not. Nevertheless, all four GFs bound $FNIII_{1-7}$, $FNIII_{1-2}$, $FNIII_{1}$ and $FNIII_{2}$, and all but VEGF bound anastellin, a 76-aa peptide within $FNIII_{1}$. These data strongly suggest a cryptic GF-binding site within the first and second type III repeat of FN. The tested biological activities of GFs bound to a FN functional domain were retained or enhanced. Our studied suggest that FN, or its fragments, may act as promiscuous cofactors for GFs and provide a novel mechanism by which GFs and ECM may accentuate the cooperativity of GF receptors and integrins on the cell surface. In addition, our studies provide important information regarding the delivery of GFs and the sequestering of GFs, as appropriate, for therapeutic (e.g., surgical) or aesthetic indications, including wound healing treatments (where an aim is GF delivery) and cancer treatments (where an aim is GF sequestration). Where FN fragments are used to deliver GFs, they may be described as maintaining, activating, stabilizing or enhancing GF activity.

Synthetic Peptides that Bind TGF-β1 and PDGF-BB

We have elucidated four homologous 25 amino acid sequences within FN. Two are within $FNIII_{1}$(peptide 1 and peptide 2), one within $FNIII_{13}$(peptide 3), and one within the FN variably-spliced IIICS (peptide 4). Their sequences are:

```
QPSHISKYILRWRPKNSVGRWKEAT;      (peptide 1;
                                 SEQ ID NO: 3)

QLISIQQYGHQEVTRFDFTTTSTST;      (peptide 2;
                                 SEQ ID NO: 4)

NGQTPIQRTIKPDVRSYTITGLQPGT;     (peptide 3;
                                 SEQ ID NO: 5)

and

QPSVGQQMIFEEHGFRRTTPPTTAT.      (peptide 4;
                                 SEQ ID NO: 6)
```

These peptides represent domains that follow the sequence pattern [QN]-X(1,2)-[ST]-X(0,1)-[IG]-[QS]-[KRQ]-[YTM]-[IG]-X(4,5)-X(0,1)-[KR]-X(1,2)-X(1,2)-[RT]-X(1,2)-[KQTS]-X(2)-T and that bind TGF-β1 with a certain affinity. Our equilibrium binding experiments indicate binding affinities of 1.3 ×$10^{-7}$ M, 2.7 ×$10^{-7}$ M, 1.4 ×$10^{-7}$ M and 1 ×$10^{\times 7}$ M, respectively. We know of no other peptides in the human genome database that follow this pattern. Peptide 1 also binds PDGF-BB (KD =2.5 ×$10^{-7}$ M) while a scrambled control does not. Further analysis of peptide 1 demonstrated that QPSHISKYILRWRPK (SEQ ID NO: 7) and ILRWRP-KNSVGRWK (SEQ ID NO: 8) bound TGF-β1 with affinities of 4.4 ×$10^{-7}$ M and 4.0 ×$10^{-7}$ M, respectively, while QPSHISKY (SEQ ID NO: 13) had minimal binding activity.

Among our objectives was the production of an acellular 3-dimensional (3-D) extracellular matrix that facilitates tissue repair through its intrinsic ability to recruit cells, such as parenchymal cells, to the site of an injury and to induce them to produce new cells and tissue(s). As noted above, the ECM can include one to three (or all three) fibronectin functional domains (FNfds), including $FNIII_{8-11}$ (C), $FNIII_{12-15}$ (H) and $FNIII_{12-v15}$ (HV), which can be constructed recombinantly as arrayed on a natural FN heterodimer and incorporated into a hydrogel (e.g., tethered to an intramolecularly crosslinked hyaluronan (HA) hydrogel). C, H and HV appear to be necessary and sufficient for optimal adult human fibroblast migration. $FNIII_{1}$, as well as H and HV, promiscuously, but selectively, bind growth factors, which retain functional activity while bound. This finding led us to believe that engineered ECM can bind GFs, whether exogenously added or endogenously generated, and thereby localize them in an active form to sites where an engineered ECM has been applied. Appropriate sites include freshly debrided ulcers (e.g., chronic ulcers), as well as surgical and traumatic wounds, including those that cannot be closed.

STUDIES PERFORMED: Fibroblast Migration is the Rate Limiting Step in Granulation Tissue Formation Using two new paradigms of acute wounds, we have previously determined that fibroblast activation and migration, rather than provisional matrix maturation, is the rate limiting step in granulation tissue development (which normally has a 3-day lag after injury). A reinjured porcine cutaneous wound model was developed to establish whether fibrin matrix maturation was the limiting step. Full-thickness wounds were allowed to heal for 5 or 7 days and then reinjured with aggressive curretting to remove all granulation tissue. A new fibrin clot formed in the re-injured wounds, which was replaced by a fibroblast-rich granulation tissue within just 24 to 48 hours. Little (~24 h) or no delay was observed in the initiation of fibroblast migration into the 5 or 7 day re-injured wounds, respectively. It is unlikely that fibrin matrix maturation was responsible for the 3-day lag in granulation tissue formation consistently observed in fresh wounds. The second paradigm was freshly made porcine skin wounds. Using this animal model, we found that addition of culture-activated skin fibroblasts plus platelet releasate or platelet-derived growth factor-BB (PDGF-BB), suspended in a human fibrin/FN gel could induce precocious granulation tissue at 3 days (i.e., the lag phase was shortened to two days). Furthermore, when fibroblasts are in an appropriate ECM context (including routine tissue culture as the cells become enmeshed in FN as they approach confluence), increases in α5β1 expression on cell surface takes approximately 24 hours after PDGF stimulation.

FN is Important for Human Fibroblast Transmigration from 3-D Collagen to Fibrin Gel in vitro and in vivo Based on our prior in vitro data, FN is critical for cell invasion of the fibrin clot. To simulate fibroblast movement from periwound collagenous stroma into provisional matrix-filled wound space, a contracted collagen gel containing skin fibroblasts was pasted onto a surface of fibrin fibrils and surrounded by a fibrin clot. This forms an "inside-out" wound environment. To further simulate the in vivo situation, 30 ng/ml PDGF was added to the fibrin clot. Fibroblast appearance in the translucent fibrin gel was quantified by cell counts. At 24 hours cell accumulation in the fibrin gel was attributable to migration rather than mitogenesis as judged by the similar accumulation of nonproliferating, irradiated cells. Transmigration from the organotypic dermal environment into fibrin required FN in both matrices. In addition, migration was dependent on α5β1 and αvβ3, integrin receptors that bind FN. Absence of FN in the provisional matrix of chronic ulcers may also hinder tissue cell accumulation in the wound. This possibility has been supported in fresh porcine wounds to which exogenous fibrin without FN was added. Relative few cells moved into these wounds compared to wounds receiving fibrin replete with FN. Thus, one of the fundamental reasons that a fresh surgical or traumatic gaping wound heals faster than a chronic ulcer may be that the former has a provisional matrix with abundant FN while the latter has little or no FN.

FN Functional Domains are Required for Improved Adult Human Dermal Fibroblast (ADHF) Migration The HA-FN provisional matrix of early granulation tissue appears to have the capacity to support robust fibroblast migration. This trait is desirable for an ECM present at a time when new tissue formation depends on robust cell movement. Since FN is required for fibroblast migration through both fibrin clots and HA gels, the FNfds required for migration were sought. From the subsequent investigations we determined that functional domains containing the cell-binding site ($FNIII_{8-11}$) (C) for α5β1 and αvβ3, the heparin II binding site ($FNIII_{12-15}$)(H) for CD44 and Syndecan 4, and the IIICS (V) sites for α4β1 were required for optimal AHDF migration. Interestingly, neonatal human fibroblast cell strains and cell lines, such as 3T3 cells or rat fibrosarcoma cells, only required the cell-binding domain ($FNIII_{8-11}$) for optimal movement, and AHDF only required $FNIII_{8-11}$ for optimal adhesion and spreading. It is known that cell movement depends on the amount of ligand and the amount of receptor available. Using human recombinant FNfds, we have demonstrated the requirement of all three domains at surface coating concentrations of 0.33 to 100 μM for optimal PDGF-stimulated AHDF migration.

Cloning and Expression of Human FN Domains

Functional human FN domains have been cloned by PCR using the human cDNA clones pFH1, pFH111 and pFH154, as templates or by subcloning of the restriction enzyme fragments from these plasmids. Clones pFH 111 and pFH 154 were purchased from the American Type Culture Collection (ATCC), while the pFH1 clone was obtained from the Japan Health Sciences Foundation. A bacterial expression vector, pETCH, was constructed by modifying the pET vector from Stratagene. The inserts were cloned at the BamHI and HindIII sites, and confirmed by DNA sequencing to rule out possible synthesis errors during PCR. Protein induction and purification procedures have been optimized for each of the FN fragments. Protein expression was induced in the BL21DE3LysS strain of E coli by the addition of 0.5 mM IPTG to the L-Broth and affinity-purified using the Ni-NTA agarose (Qiagen) according to the manufacturer's protocol. After elution with 250 mM imidazole, the protein solution was purified in a G25 gel filtration column equilibrated in PBS, and the aliquots stored at −70° C. The PCR products were purified and digested with restriction enzymes. The restriction fragments are separated by gel electrophoresis, purified, ligated into the vector, and transformed into competent bacteria DH5α. The clones are confirmed by DNA sequencing, and transformed into BL21DE3-LysS bacteria for protein purification. In addition, we have cloned and expressed $FNIII_{1-11}$, $FNIII_{1-2}$, $FNIII_1$, $FNIII_2$, $FNIII_{3-6}$, and $FNIII_{12-14}$. The recombinant FN functional domains have three extra amino acids (MetGlySer) at the N-terminus and seven to eight extra amino acids (ThrSerHisHisHisHisHisHisCys (SEQ ID NO: 12)) at the C-terminus (Thr is naturally present at the end of type III repeat 11 and EDA). In some constructs, the coding sequence of glutathione S-transferase (GST) was inserted at the C-terminus.

Engineered ECM Platforms

We have engineered an intramolecularly cross-linked HA hydrogel matrix that is tethered with FNfds C, H and HV for improved fibroblast migration in in vitro models and in vivo wound healing. The engineered ECM also provides a useful 3-D complex ECM for studies on cell responses to complex ECM containing different FNfds. Rapid (within just 18 hours) and robust migration of adult human dermal fibroblasts (AHDFs) occurred on engineered ECM peaking at a FNfd density of 0.26 μM in a typical bell-shaped manner. Migration appeared to occur en masse rather than as single cells. AHDF spreading and proliferation also reached 90% of maximal at 0.26 μM. Thus, 0.26 μM appeared optimal for FNfds stimulation of AHDF functional responses.

After obtaining the optimum FNfds bulk densities (268 nM) and crosslinking ratios (2:1) from in vitro functional studies, we tested our engineered ECM in vivo in a porcine re-injury model. The wounds of a porcine re-injury model contain a large population of activated periwound tissue fibroblasts that transform from the (usual) stationary phenotype into a migratory one that facilitates granulation tissue formation. Therefore, this re-injury model is suited mainly to identify any adverse effect(s) of a wound additive, which would compromise this migratory phenotype of the stimulated periwound fibroblasts. Before use in vivo, the FNfd-SH solutions were treated with deToxi gel (Pierce, IL) to remove endotoxins. Punch biopsy (8 mm; full-thickness) wounds created in female Yorkshire pigs were covered with Tegaderm® (and allowed to heal spontaneously for 5 days. Thereafter, the granulation tissue was curetted out, creating fresh wounds. Sterile, endotoxin-free HA hydrogels coupled with C, H and HV, HA hydrogels without FNfds, and HA hydrogels coupled with RGD were added to the wounds as pre-gelling solutions that gelled in situ within 9 minutes. Five wounds received no HA hydrogels and were treated as controls.

When the specimens were harvested at two days post-implantation and analyzed histologically, we observed essentially no signs of acute inflammation, suggesting the overall biocompatibility of engineered ECM. More remarkably, wounds receiving these acellular engineered ECM hydrogels showed rapid fibroblast migration and profound granulation tissue formation (90% wound space filled) within just two days. In contrast, wounds filled with either HA-DTPH-PEGDVS-RGD showed marked inhibition of granulation tissue formation. These results suggest, first, that C, H and HV are instrumental in facilitating the recruitment of host tissue fibroblasts into acellular engineered ECM and, second, once migrated into the wounds, recruited fibroblasts assume normal tissue phenotype by depositing in situ collagen (as detected by trichrome blue staining) which demonstrates inductive properties of FNfds. In addition, the engineered ECM hydrogels also encouraged reepithelialization by stimulating keratinocyte migration.

Next, engineered ECM were implanted into "regular" porcine wounds immediately after wounding. Tissue samples were harvested and analyzed at 3, 4, 5 and 7 days. From a power analysis we determined that 6 replicates for each condition were sufficient to obtain statistical differences at 95% confidence if the variance among replicates was <20%. All HA hydrogels were endotoxin-free and implanted in a manner that accounts for the regional differences in tissue ingrowth between the dorsal/ventral or anterior/posterior ends. The harvested wound specimens were stained with trichrome blue for histological analysis to delineate morphological alterations in the granulation tissue. No granulation tissue had accumulated in 3 day wounds regardless of treatment (i.e., no treatment), HA hydrogels at crosslinking ratios of 2:1 without FN functional domains, 268 µM RGD tethered to HA hydrogels, or engineered ECM decorated with C, H, and HV at final bulk densities of 268 nM each. Wounds four days after injury, however, demonstrated statistically significant differences in healing only among wounds containing engineered ECM+PDGF versus wounds receiving no treatment or blank HA hydrogels (P<0.001 by one way ANOVA and Tukey post hoc analysis). The best results occurred in wounds receiving engineered ECM that was decorated with C, H, and HV and preloaded with 100 ng/ml of PDGF-BB. This was particularly intriguing since the final amount of PDGF-BB added to each of these wounds was only ~15 ng (~150 µL of hydrogel per wound containing 100 ng/ml PDGF-BB), which is a 30-3000 fold lower dose than what was previously reported to produce significant accentuation. By 5 and 7 days, wounds were on average filled with granulation tissue at 75% and 100% of total wound, respectively, with no differences noted among experimental conditions.

The extent of re-epithelialization was also determined from the histological sections. Since Masson trichrome stains tissue cells pink, the migrating epidermal tongue was easily detected and traced for quantitative analysis. Similar to granulation tissue, percent re-epithelialization was increased by FNfd-derivatized xHA, in contrast to non-derivatized xHA, with the greatest accentuation produced by xHA-FNfd+PDGF-BB. xHA-FNfd hydrogels alone showed an increase, albeit insignificant, in percent re-epithelialization.

Angiogenesis was also determined from histological evaluation of sections from these experiments. CD31, or PECAM-1, is a characteristic endothelial cell adhesion molecule that is expressed on its surface and plays a role in angiogenesis. Laminin is an ECM protein found in the basal laminae of mature capillaries. When we double-labeled day 4 wound sections with anti-CD31 and anti-laminin, we found that all CD31-positive structures were colocalized with laminin, indicating that the capillaries had matured. The nearly vertical alignment of the new capillaries is typical of wound angiogenesis and is due to endothelial cell migration towards the major source of vascular endothelial growth factor (VEGF), the epidermal cells. Similar to a recently reported technique, the quantitative analysis of angiogenesis was performed by measuring the percent area of wound granulation tissue that was occupied by the new capillaries. All wound additives accentuated angiogenesis above the "no treatment" control, with the xHA-FNfd±PDGF-BB hydrogels showing a 2-fold increase. Unlike the effects seen in granulation tissue accumulation and re-epithelialization, PDGF-BB failed to significantly enhance angiogenesis observed with xHA-FNfd alone. Both xHA-FNfd±PDGF hydrogels showed marked increase in percent neovascularization over xHA-RGD+PDGF hydrogels.

FN Domains Bind PDGF-BB

PDGF is a potent chemoattractant and mitogen for fibroblasts, promotes healing of soft tissue wounds and is approved by the U.S. Food and Drug Administration for treatment of chronic cutaneous ulcers. Interestingly, we observed that as little as 100 ng/ml (15 ng total per wound) PDGF-BB added to 2:1 engineered ECM enhanced granulation formation at 4 days after injury and application of material.

This led us to speculate that PDGF was binding to the engineered ECM through the H or HV domain since vascular endothelial GF (VEGF), a member of the PDGF superfamily, had been reported to bind H and remain active while bound. Equilibrium binding studies and surface plasmon resonance were utilized to assay amino- to carboxy-terminal FN domains (FN70, $FNIII_{1-7}$, $FNIII_{8-11}$ (C), and $FNIII_{12-V15}$ (HV) for PDGF binding activity. $FNIII_{1-7}$ and HV were found to have strong binding affinities for PDGF-BB (KD=7.5× $10^{-8}$ M, KD=2.1×$10^{-8}$ M, respectively) while the 70 kDa amino terminus of FN (FN70), which includes fibrin and gelatin binding domains and C ($FNIII_{8-11}$) did not. Plasmon surface resonance kinetic binding confirmed these results (KD=1.0×$10^{-7}$ M, KD=1.7×$10^{-8}$M, respectively). Compared to PDGF-BB binding to $FNIII_{12-V15}$ (KD=2.1×$10^{-8}$ M), similar equilibrium binding was observed to $FNIII_{12-15}$ (KD=6.8× $10^{-9}$ M), $FNIII_{12-14}$ (KD=3.5×$10^{-8}$ M) and $FNIII_{12-13}$ (K=7.5×$10^{-8}$ M) and somewhat weaker binding to IIICS (KD=3.5×$10^{-7}$ M). Interestingly, GFs binding to $FNIII_{12-V15}$ (HV) failed to demonstrate any diminution when up to 2.5 M NaCl was added or when pH was lowered to about 2.0 strongly indicating that charge is not required for the interaction.

As judged by equilibrium binding, $FNIII_1$ and $FNIII_{1-2}$ bound PDGF-BB (KD=3.2×$10^{-8}$ M, 3.7×$10^{-8}$ M, respectively), while $FNIII_{3-6}$ did not. Plasma surface resonance confirmed these findings: $FNIII_1$ (KD=3.7×$10^{-7}$ M), $FNIII_{1-2}$ (KD=9.1×$10^{-9}$ M), and no binding with $FNIII_{3-6}$.

Four Homologous Peptides within 3 FN Domains Bind PDGF-BB

To further localize PDGF-BB binding within $FNIII_1$, we acquired a peptide from the central 76 amino acids (aa) of $FNIII_1$ (FN630-704), which has anti-angiogenic properties and promotes FN polymerization. This peptide as well as its two halves, FN630-667 and FN668-704, demonstrated PDGF-BB binding. Next, we looked for sequence homologies within the two halves of the peptide and discovered the sequence pattern noted above ([QN]-X(1,2)-[ST]-X(0,1)-[IG]-[QS]-[KRQ]-[YTM]-[IG]-X(4,5)-X(0,1)-[KR]-X(1,2)-X(1,2)-[RT]-X(1,2)-[KQTS]-X(2)-T) (see peptides 1-4). The four homologous peptides demonstrated binding with PDGF-BB while scrambled variants did not. These findings may explain similar PDGF-BB binding among FN heparin-binding domains, $FNIII_{12-V15}$, $FNIII_{12-15}$, $FNIII_{12-14}$, $FNIII_{12-13}$, and IIICS. Smaller peptides from $FNIII_1$ revealed PDGF-BB binding with FN630-648:WNAPQPSHISKYIL-RWRPK SEQ ID NO: 14; KD=3.4 $\times10^{-7}$ M) and a 15 as peptide FN634-648: QPSHISKYILRWRPK (SEQ ID NO:7; KD=4.5 $\times10^{-7}$ M), but not with the 8 as peptide FN634-641: QPSHISKY (SEQ ID NO: 13), nor FN641-654:YILRWRP-KNSVGRW (SEQ ID NO: 15), nor FN648-667:KNSVGR-WKEATIPGHLNSYT (SEQ ID NO: 16).

Next, we determined if PDGF-BB-binding peptides from $FNIII_1$ could inhibit PDGF-BB binding to $FNIII_1$, $FNIII_{12-14}$ and IIICS. For initial experiments we selected peptide 1 and peptide 2. For control, we used scrambled peptide 1. Although peptide 1 showed marked inhibition of PDGF-BB binding to all three FN domains, neither peptide 2, nor the scramble varient of peptide 1 (FN634-658s), demonstrated inhibition of PDGF-BB binding to any of the FN domains. We noted that peptide 1 bound PDGF-BB with slightly less affinity than peptide 2 (KD=2.5$\times10^{-7}$ M, KD=1.1$\times10^{-7}$ M, respectively).

PDGF-BB Bound to $FNIII_{1-2}$, $FNIII_{12-15}$ (HV) or $FNIII_{12-15}$ (HV) retains Biological Activity To determine whether PDGF-BB, bound to recombinant FN domains, remained active, we investigated the migratory response of AHDF to 100 ng/ml PDGF-BB preloaded for two hours in engineered ECM containing C, H, and HV (268 nM bulk density, each) versus PDGF-BB preloaded on engineered ECM containing only C. Preloading was followed by 10 washes with DMEM. For each wash the engineered ECM was gently agitated on an orbital shaker for 5 minutes. The last wash had little or no detectable PDGF motogenic activity. As a positive control, PDGF-BB was added to the medium of both engineered ECM constructs. Fibroblasts migrated as well to PDGF-BB preloaded on engineered ECM tethered with C, H and HV as to PDGF-BB added to the culture medium. In contrast, no fibroblast migration occurred when PDGF was preloaded on engineered ECM containing C alone although cell migration on engineered ECM tethered with C responded well when PDGF was added to the medium. In other experiments, PDGF was preloaded on engineered ECM containing C alone or C plus $FNIII_{1-2}$. Fibroblasts migrated as well to PDGF-BB preloaded on engineered ECM tethered with C plus $FNIII_{1-2}$ as to PDGF-BB added to the culture medium. Similar data was acquired when human dermal microvascular endothelial cells (HDMEC) were used in these migration assays and either PDGF-BB or bFGF were preloaded on engineered ECM tethered with C alone or C in combination with H and HV or $FNIII_{1-2}$.

FN-nullfibroblasts require the FN central cell-binding domain & a PDGF-binding domain for survival.

To further investigate the response of cells to PDGF-BB bound to FN domains, we investigated the survival response of mouse fibroblasts null for FN (FN−/−). First we determined the response of FN-null cells to PDGF-BB in the absence of serum or other sources of exogenous FN. When PDGF was added 1 day after plating, FN-null cells failed to survive in the presence of PDGF while mouse cells heterozygous for FN (FN−/+) demonstrate increasing cell numbers to increasing concentrations of PDGF. Next, FN-null cells were plated on tissue culture plastic surfaces precoated with 0.15 μM GST-tagged $FNIII_{8-11}$± other FN domains known to have PDGF-BB binding activity and then PDGF-BB added 1 day later. On $FNIII_{8-11}$+FN domains with PDGF-BB binding activity (i.e., $FNIII_1$, $FNIII_{12-14}$ or IIICS, FN-null cells demonstrated increased survival with PDGF at 3 days while cells failed to survive on $FNIII_{8-11}$ alone. The best survival response was observed when cells were plated on $FNIII_{1-11}$, which contains the $FNIII_1$ PDGF-binding domain in contiguous array with the $FNIII_{8-11}$ cell-binding domain. Similar results were observed when FNnull cells were plated on intact FN. Furthermore, cells survived on $FNIII_{1-11}$ even in the absence of PDGF-BB suggesting perhaps that the cells load endogenous PDGF on FN PDGF-binding domains. Importantly, differential response of FN-null cells, plated on different FN domains, to PDGF-BB was not secondary to differences in attachment as judged by cell counts two hours after plating. The $FNIII_{8-11}$ central cell binding domain was present in all circumstances. When PDGF-BB was added to FN-null cells 2 hrs after plating, they showed enhance survival on $FNIII_{8-11}$+$FNIII_{1-2}$, $FNIII_{12-14}$, $FNIII_{12-V15}$ or IIICS, but not $FNIII_{8-11}$ alone or $FNIII_{8-11}$+$FNIII_{3-6}$, and robust proliferation on intact FN, $FNIII_{1-11}$ or $FNIII_{8-V15}$.

Intact FN Provides Promiscuous, But Selective, GF-Binding Sites

The survival of FN-null fibroblasts in the presence to PDGF-BB required substrate coated with intact FN or $FNIII_{8-11}$+a PDGF-binding FN domain. $FNIII_{8-11}$ alone and $FNIII_{8-11}$+$FNIII_{3-6}$ did not support cell survival. These data strongly suggest that PDGF-BB binds intact FN. That is, PDGF-BB binding sites on FN are not cryptic as demonstrated for FN self-association sites. To address this directly, we performed equilibrium binding assays with PDGF-BB to FN adsorbed to a surface or coupled to agarose beads. In addition, we also investigated the ability of other growth factors to bind intact FN. PDGF-BB (KD=4.9$\times10^{-8}$ M), TGF-β1 (KD=5.3$\times10^{-8}$ M) and bFGF (KD=4.4$\times10^{-8}$ M) bound intact FN while EGF, TGF-α and FGF-1 did not.

TGF-β1 and bFGF Binds the Same FN Domains and Peptides as PDGF-BB

To determine whether FN domains bind TGF-β1 and bFGF, equilibrium and kinetic binding was performed. TGF-β1 bound FNIII1-7 (KD=1.7$\times10^{-8}$ M) and FNIII12-V15 (KD=9.7$\times10^{-8}$ M), but not FN70 nor FNIII 8-11, as previously observed with PDGF-BB. Kinetic binding via plasmon surface resonance confirmed these findings (KD=1.8$\times10^{-8}$ M, KD=2.5$\times10^{-8}$ M, respectively). Similar data was acquired with bFGF, which bound to $FNIII_{1-7}$ (KD=4.1$\times10^{-9}$ M) and $FNIII_{12-V15}$ (KD=3.7$\times10^{-8}$ M), but not FN70 nor $FNIII_{8-11}$. EGF, TGF-α and FGF-1 failed to bind to any these FN domains.

Furthermore, $FNIII_1$, $FNIII_{12-14}$, $FNIII_{12-15}$ and IIICS, but not $FNIII_{3-6}$, also bound TGF-β1 (KD=6.2$\times10^{-9}$ M, 7.6$\times10^{-9}$ M, 1.6$\times10^{-8}$ M, 7.4$\times10^{-8}$ M, respectively) and bFGF (KD=3.5$\times10^{-8}$ M, 1.9$\times10^{-9}$ M, 1.3$\times10^{-7}$ M, 5.8$\times10^{-8}$ M, respectively). Peptides 1-4 could bind TGF-β1 and bFGF and peptide 1 completely inhibited TGF-β1 and bFGF binding to any recombinant FN domain as shown for PDGF-BB. Once again, EGF, TGF-α and FGF-1 failed to bind to any recombinant FN domain or synthetic peptide. In no case did any GF bind the 70 kDa amino terminus of FN domain (FN70), which includes the fibrin I and gelatin binding domains, nor $FNIII_{3-6}$, nor $FNIII_{8-11}$ (the central cell binding domain, C).

TGF-β1 or bFGF Bound to FNIII1-2 and FNIII12-V15 Retains Biological Activity

Although TGF-β1 has been reported to bind directly to decorin, a proteoglycan found in connective tissue including the dermis, and to FN through latent TGF-β binding protein LTBP-2, the TGF-β1 is inactive while bound to these ECM molecules. TGF-β that adhered to FN retained full functional activity as judged by inhibition of [³H]-thymidine incorporation by CCL-64 mink lung cells, as described in the literature. Therefore, we investigated whether it retained its activity while bound to recombinant FN functional domains. $FNIII_{8-11}$ was adsorbed on plastic tissue culture dishes at a surface density to maximally affect the attachment and spreading of human dermal fibroblasts with or without the presence of adsorbed $FNIII_{1-2}$. Fibroblasts cultured in plates coated with both $FNIII_{8-11}$ and $FNIII_{1-2}$ produced type 1 collagen in a dose response fashion to increasing concentrations of TGF-β1 that had been preincubated with the FN domain coated plates. The maximum collagen secretion was approximately 25% of the amount observed when TGF-β1 remained in the medium at the concentrations indicated. No increase in collagen synthesis was observed when fibroblasts were cultured in plates that were coated with $FNIII_{8-11}$ alone and then preincubated with TGF-β1. The numbers of attached and spread cells were essentially identical when fibroblasts were cultures on plates coated with both FNIII8-11 and FNIII1-2 or FNIII8-11 alone. Similar data was obtained when fibroblasts were cultured on plates that had been coated with FNIII8-11 and FNIII12-V15 and then preincubated with TGF-β1.

To determine whether FN functional domains modulated TGF-β1, bFGF or PDGF-BB activity in solution, fibroblast chemotaxis was performed in response to the GFs in the presence or absence of FN domains. Although FNIII1-2 and FNIII12-V15 had no chemotactic activity when assayed alone, they both enhanced the chemotactic activity of TGF-β1, bFGF and PDGF-BB. In contrast, $FNIII_{3-6}$ did not enhance fibroblast chemotaxis.

In preliminary results investigating signal transduction pathway activation of growth factors in the presence of FN GF-binding peptides, the response of ERK to PDGF-BB in the presence and absence of FNIII1-2 was studied. Without FNIII1-2, the ERK response to PDGF-BB was maximum at 20 minutes and gradually diminished over four hrs. In the presence of FNIII 1-2, the ERK response to PDGF-BB, was about 25% greater and sustained for at least four hours.

From these data, we posit that the FN central cell-binding domain $FNIII_{8-11}$ (C) is flanked by at least four promiscuous, but selective, GF-binding sites, two in FNIII1 (peptide 1 and 2), one in FNIII 13 (peptide 3) and one in IIICS (peptide 4). Furthermore, it appears that GFs bound to FN GF-binding domains on a surface, or in solution, remain active or even enhanced. When GFs are bound to FN ECM, integrin receptor ligation of FN can lead to not only integrin aggregation, but also the aggregation of GF receptors into focal contacts setting the stage for solid-phase stimulation of cells with GFs prebound to FN.

Although others have reported that IGF binds indirectly and VEGF binds directly to the HepII domain ($FNIII_{12-15}$) of FN, no reports exist regarding the binding of active TGFβ or PDGF to FN functional domains and whether these GFs retain activity while bound. Furthermore, it has been reported that fibstatin, the 12-14th type III repeats of FN, binds and inhibits the biologic activity of bFGF. The data presented here demonstrate that TGF-β1 and β2, PDGF-BB and bFGF bind anastellin, $FNIII_{1-2}$, $FNIII_{12-15}$ or $FNIII_{12-V15}$ with relatively high affinity (KDs from $10^{-8}$ to $10^{-9}$). The finding that these GFs bind the anastellin and $FNIII_{1-2}$ is unexpected, as this domain has had a paucity of functions ascribed to it until recently.

A number of embodiments of the invention have been described. Nevertheless, it will be understood that various modifications may be made without departing from the spirit and scope of the invention. Accordingly, other embodiments are within the scope of the following claims.

What is claimed is:

1. A method of promoting wound healing in a patient, the method comprising administering to the patient a therapeutically effective amount of a pharmaceutical or physiologically acceptable composition comprising a polypeptide, wherein the polypeptide consists of the amino acid sequence QPSHISKYILRWRPK (SEQ ID NO:7).

2. The method of claim 1, wherein the pharmaceutical or physiologically acceptable composition is formulated for topical administration.

3. The method of claim 1, wherein the patient is suffering from a laceration, burn, or ulceration of the skin.

4. A method of promoting wound healing in a patient, the method comprising administering to the patient a therapeutically effective amount of a pharmaceutical or physiologically acceptable composition comprising a polypeptide, wherein the polypeptide consists of the amino acid sequence QPSHISKYILRWRPK (SEQ ID NO:7) having two additional cysteine residues, a first cysteine residue at the N-terminus and a second cysteine residue at the C-terminus.

5. The method of claim 4, wherein the polypeptide is in a cyclic form.

6. The method of claim 4, wherein the pharmaceutical or physiologically acceptable composition is formulated for topical administration.

7. The method of claim 4, wherein the patient is suffering from a laceration, burn, or ulceration of the skin.

8. A method of promoting wound healing in a patient, the method comprising administering to the patient a therapeutically effective amount of a pharmaceutical or physiologically acceptable composition comprising a polypeptide, wherein the polypeptide consists of the amino acid sequence QPSHISKYILRWRPK (SEQ ID NO:7) and a heterologous sequence that increases the circulating half-life of the polypeptide.

9. The method of claim 8, wherein the heterologous sequence that increases the circulating half-life of the polypeptide is an albumin or a portion of an immunoglobulin.

10. The method of claim 9, wherein the albumin is a human serum albumin or a portion thereof and the portion of an immunoglobulin is the Fc region of an IgG.

11. The method of claim 8, wherein the pharmaceutical or physiologically acceptable composition is formulated for topical administration.

12. The method of claim 8, wherein the patient is suffering from a laceration, burn, or ulceration of the skin.

* * * * *

SEQUENCE LISTING

<160> NUMBER OF SEQ ID NOS: 18

<210> SEQ ID NO 1
<211> LENGTH: 2386
<212> TYPE: PRT
<213> ORGANISM: Homo sapiens

<400> SEQUENCE: 1

Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly

-continued

```
                130                 135                 140
Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
                275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
                370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560
```

-continued

```
Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990
```

```
Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Arg Ala Gln Ile
1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
            1075                1080                1085

Ser Ser Ile Pro Pro Tyr Asn Thr Glu Val Thr Glu Thr Thr Ile Val
            1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
            1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
            1235                1240                1245

Thr Val Lys Asp Asp Lys Glu Ser Val Pro Ile Ser Asp Thr Ile Ile
            1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
                1285                1290                1295

Asn Phe Leu Val Arg Tyr Ser Pro Val Lys Asn Glu Glu Asp Val Ala
                1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
                1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
```

```
                1410                1415                1420
Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
                1460                1465                1470

Val Thr Val Arg Tyr Tyr Arg Ile Thr Tyr Gly Glu Thr Gly Gly Asn
                1475                1480                1485

Ser Pro Val Gln Glu Phe Thr Val Pro Gly Ser Lys Ser Thr Ala Thr
                1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
                1540                1545                1550

Val Gln Asp Asn Ser Ile Ser Val Lys Trp Leu Pro Ser Ser Ser Pro
                1555                1560                1565

Val Thr Gly Tyr Arg Val Thr Thr Thr Pro Lys Asn Gly Pro Gly Pro
                1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Asn Ile
                1620                1625                1630

Asp Arg Pro Lys Gly Leu Ala Phe Thr Asp Val Asp Val Asp Ser Ile
                1635                1640                1645

Lys Ile Ala Trp Glu Ser Pro Gln Gly Gln Val Ser Arg Tyr Arg Val
                1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
                1685                1690                1695

Glu Tyr Thr Val Ser Val Val Ala Leu His Asp Asp Met Glu Ser Gln
                1700                1705                1710

Pro Leu Ile Gly Thr Gln Ser Thr Ala Ile Pro Ala Pro Thr Asp Leu
                1715                1720                1725

Lys Phe Thr Gln Val Thr Pro Thr Ser Leu Ser Ala Gln Trp Thr Pro
                1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
                1765                1770                1775

Val Val Val Ser Gly Leu Met Val Ala Thr Lys Tyr Glu Val Ser Val
                1780                1785                1790

Tyr Ala Leu Lys Asp Thr Leu Thr Ser Arg Pro Ala Gln Gly Val Val
                1795                1800                1805

Thr Thr Leu Glu Asn Val Ser Pro Pro Arg Arg Ala Arg Val Thr Asp
                1810                1815                1820

Ala Thr Glu Thr Thr Ile Thr Ile Ser Trp Arg Thr Lys Thr Glu Thr
1825                1830                1835                1840
```

-continued

```
Ile Thr Gly Phe Gln Val Asp Ala Val Pro Ala Asn Gly Gln Thr Pro
            1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
            1875                1880                1885

Asn Ala Arg Ser Ser Pro Val Val Ile Asp Ala Ser Thr Ala Ile Asp
            1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
            1925                1930                1935

Tyr Glu Lys Pro Gly Ser Pro Pro Arg Glu Val Val Pro Arg Pro Arg
            1940                1945                1950

Pro Gly Val Thr Glu Ala Thr Ile Thr Gly Leu Glu Pro Gly Thr Glu
            1955                1960                1965

Tyr Thr Ile Tyr Val Ile Ala Leu Lys Asn Asn Gln Lys Ser Glu Pro
            1970                1975                1980

Leu Ile Gly Arg Lys Lys Thr Asp Glu Leu Pro Gln Leu Val Thr Leu
1985                1990                1995                2000

Pro His Pro Asn Leu His Gly Pro Glu Ile Leu Asp Val Pro Ser Thr
            2005                2010                2015

Val Gln Lys Thr Pro Phe Val Thr His Pro Gly Tyr Asp Thr Gly Asn
            2020                2025                2030

Gly Ile Gln Leu Pro Gly Thr Ser Gly Gln Gln Pro Ser Val Gly Gln
            2035                2040                2045

Gln Met Ile Phe Glu Glu His Gly Phe Arg Arg Thr Thr Pro Pro Thr
            2050                2055                2060

Thr Ala Thr Pro Ile Arg His Arg Pro Arg Pro Tyr Pro Pro Asn Val
2065                2070                2075                2080

Gly Glu Glu Ile Gln Ile Gly His Ile Pro Arg Glu Asp Val Asp Tyr
            2085                2090                2095

His Leu Tyr Pro His Gly Pro Gly Leu Asn Pro Asn Ala Ser Thr Gly
            2100                2105                2110

Gln Glu Ala Leu Ser Gln Thr Thr Ile Ser Trp Ala Pro Phe Gln Asp
            2115                2120                2125

Thr Ser Glu Tyr Ile Ile Ser Cys His Pro Val Gly Thr Asp Glu Glu
            2130                2135                2140

Pro Leu Gln Phe Arg Val Pro Gly Thr Ser Thr Ser Ala Thr Leu Thr
2145                2150                2155                2160

Gly Leu Thr Arg Gly Ala Thr Tyr Asn Ile Ile Val Glu Ala Leu Lys
            2165                2170                2175

Asp Gln Gln Arg His Lys Val Arg Glu Glu Val Val Thr Val Gly Asn
            2180                2185                2190

Ser Val Asn Glu Gly Leu Asn Gln Pro Thr Asp Asp Ser Cys Phe Asp
            2195                2200                2205

Pro Tyr Thr Val Ser His Tyr Ala Val Gly Asp Glu Trp Glu Arg Met
            2210                2215                2220

Ser Glu Ser Gly Phe Lys Leu Leu Cys Gln Cys Leu Gly Phe Gly Ser
2225                2230                2235                2240

Gly His Phe Arg Cys Asp Ser Ser Arg Trp Cys His Asp Asn Gly Val
            2245                2250                2255

Asn Tyr Lys Ile Gly Glu Lys Trp Asp Arg Gln Gly Glu Asn Gly Gln
            2260                2265                2270
```

```
Met Met Ser Cys Thr Cys Leu Gly Asn Gly Lys Gly Glu Phe Lys Cys
        2275                2280                2285

Asp Pro His Glu Ala Thr Cys Tyr Asp Asp Gly Lys Thr Tyr His Val
    2290                2295                2300

Gly Glu Gln Trp Gln Lys Glu Tyr Leu Gly Ala Ile Cys Ser Cys Thr
2305                2310                2315                2320

Cys Phe Gly Gly Gln Arg Gly Trp Arg Cys Asp Asn Cys Arg Arg Pro
            2325                2330                2335

Gly Gly Glu Pro Ser Pro Glu Gly Thr Thr Gly Gln Ser Tyr Asn Gln
        2340                2345                2350

Tyr Ser Gln Arg Tyr His Gln Arg Thr Asn Thr Asn Val Asn Cys Pro
            2355                2360                2365

Ile Glu Cys Phe Met Pro Leu Asp Val Gln Ala Asp Arg Glu Asp Ser
        2370                2375                2380

Arg Glu
2385

<210> SEQ ID NO 2
<211> LENGTH: 75
<212> TYPE: PRT
<213> ORGANISM: Artificial Sequence
<220> FEATURE:
<223> OTHER INFORMATION: Derived from a human plasma fibronectin

<400> SEQUENCE: 2

Trp Asn Ala Pro Gln Pro Ser His Ile Ser Lys Tyr Ile Leu Arg Trp
1               5                   10                  15

Arg Pro Lys Asn Ser Val Gly Arg Trp Lys Glu Ala Thr Ile Pro Gly
            20                  25                  30

His Leu Asn Ser Tyr Thr Ile Lys Gly Leu Lys Pro Gly Val Val Tyr
        35                  40                  45

Glu Gly Gln Leu Ile Ser Ile Gln Gln Tyr Gly His Gln Glu Val Thr
    50                  55                  60

Arg Phe Asp Phe Thr Thr Thr Ser Thr Ser Thr
65                  70                  75

<210> SEQ ID NO 3
<211> LENGTH: 25
<212> TYPE: PRT
<213> ORGANISM: Artificial Sequence
<220> FEATURE:
<223> OTHER INFORMATION: Derived from a human plasma fibronectin

<400> SEQUENCE: 3

Gln Pro Ser His Ile Ser Lys Tyr Ile Leu Arg Trp Arg Pro Lys Asn
1               5                   10                  15

Ser Val Gly Arg Trp Lys Glu Ala Thr
            20                  25

<210> SEQ ID NO 4
<211> LENGTH: 25
<212> TYPE: PRT
<213> ORGANISM: Artificial Sequence
<220> FEATURE:
<223> OTHER INFORMATION: Derived from a human plasma fibronectin

<400> SEQUENCE: 4

Gln Leu Ile Ser Ile Gln Gln Tyr Gly His Gln Glu Val Thr Arg Phe
1               5                   10                  15

Asp Phe Thr Thr Thr Ser Thr Ser Thr
            20                  25
```

```
            20                  25

<210> SEQ ID NO 5
<211> LENGTH: 26
<212> TYPE: PRT
<213> ORGANISM: Artificial Sequence
<220> FEATURE:
<223> OTHER INFORMATION: Derived from a human plasma fibronectin

<400> SEQUENCE: 5

Asn Gly Gln Thr Pro Ile Gln Arg Thr Ile Lys Pro Asp Val Arg Ser
 1               5                  10                  15

Tyr Thr Ile Thr Gly Leu Gln Pro Gly Thr
            20                  25

<210> SEQ ID NO 6
<211> LENGTH: 25
<212> TYPE: PRT
<213> ORGANISM: Artificial Sequence
<220> FEATURE:
<223> OTHER INFORMATION: Derived from a human plasma fibronectin

<400> SEQUENCE: 6

Gln Pro Ser Val Gly Gln Gln Met Ile Phe Glu Glu His Gly Phe Arg
 1               5                  10                  15

Arg Thr Thr Pro Pro Thr Thr Ala Thr
            20                  25

<210> SEQ ID NO 7
<211> LENGTH: 15
<212> TYPE: PRT
<213> ORGANISM: Artificial Sequence
<220> FEATURE:
<223> OTHER INFORMATION: Synthetically generated peptide

<400> SEQUENCE: 7

Gln Pro Ser His Ile Ser Lys Tyr Ile Leu Arg Trp Arg Pro Lys
 1               5                  10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 8

Ile Leu Arg Trp Arg Pro Lys Asn Ser Val Gly Arg Trp Lys
 1               5                  10

<210> SEQ ID NO 9
<211> LENGTH: 27
<212> TYPE: PRT
<213> ORGANISM: Artificial Sequence
<220> FEATURE:
<223> OTHER INFORMATION: Synthetically generated peptide

<400> SEQUENCE: 9

Thr Ser Thr Ser Thr Thr Thr Phe Asp Phe Asp Phe Arg Thr Val Glu
 1               5                  10                  15

Gln His Gly Tyr Gln Gln Ile Ser Ile Leu Gln
            20                  25

<210> SEQ ID NO 10
<211> LENGTH: 28
<212> TYPE: PRT
```

```
<213> ORGANISM: Artificial Sequence
<220> FEATURE:
<223> OTHER INFORMATION: Synthetically generated peptide

<400> SEQUENCE: 10

Lys Lys Lys Gln Leu Ile Ser Ile Gln Gln Tyr Gly His Gln Glu Val
1               5                   10                  15

Thr Arg Phe Asp Phe Thr Thr Thr Ser Thr Ser Thr
            20                  25

<210> SEQ ID NO 11
<211> LENGTH: 28
<212> TYPE: PRT
<213> ORGANISM: Artificial Sequence
<220> FEATURE:
<223> OTHER INFORMATION: Synthetically generated peptide

<400> SEQUENCE: 11

Gln Leu Ile Ser Ile Gln Gln Tyr Gly His Gln Glu Val Thr Arg Phe
1               5                   10                  15

Asp Phe Thr Thr Thr Ser Thr Ser Thr Lys Lys Lys
            20                  25

<210> SEQ ID NO 12
<211> LENGTH: 9
<212> TYPE: PRT
<213> ORGANISM: Artificial Sequence
<220> FEATURE:
<223> OTHER INFORMATION: Synthetically generated peptide

<400> SEQUENCE: 12

Thr Ser His His His His His His Cys
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetically generated peptide

<400> SEQUENCE: 13

Gln Pro Ser His Ile Ser Lys Tyr
1               5

<210> SEQ ID NO 14
<211> LENGTH: 19
<212> TYPE: PRT
<213> ORGANISM: Artificial Sequence
<220> FEATURE:
<223> OTHER INFORMATION: Synthetically generated peptide

<400> SEQUENCE: 14

Trp Asn Ala Pro Gln Pro Ser His Ile Ser Lys Tyr Ile Leu Arg Trp
1               5                   10                  15

Arg Pro Lys

<210> SEQ ID NO 15
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 15

Tyr Ile Leu Arg Trp Arg Pro Lys Asn Ser Val Gly Arg Trp
```

```
<210> SEQ ID NO 16
<211> LENGTH: 20
<212> TYPE: PRT
<213> ORGANISM: Artificial Sequence
<220> FEATURE:
<223> OTHER INFORMATION: Synthetically generated peptide

<400> SEQUENCE: 16

Lys Asn Ser Val Gly Arg Trp Lys Glu Ala Thr Ile Pro Gly His Leu
 1               5                  10                  15

Asn Ser Tyr Thr
            20

<210> SEQ ID NO 17
<211> LENGTH: 4
<212> TYPE: PRT
<213> ORGANISM: Artificial Sequence
<220> FEATURE:
<223> OTHER INFORMATION: Synthetically generated peptide

<400> SEQUENCE: 17

Leu Arg Trp Arg
 1

<210> SEQ ID NO 18
<211> LENGTH: 5
<212> TYPE: PRT
<213> ORGANISM: Artificial Sequence
<220> FEATURE:
<223> OTHER INFORMATION: Synthetically generated peptide

<400> SEQUENCE: 18

Leu Arg Trp Arg Pro
 1               5
```